US012697292B2

(12) United States Patent
Jaiser et al.

(10) Patent No.: US 12,697,292 B2
(45) Date of Patent: Aug. 4, 2026

(54) METHOD FOR TREATING HUMAN HAIR WITH AGENTS CONTAINING MIXTURES OF ORGANIC $C_1$-$C_6$ ALKOXY SILOXANES

(71) Applicant: Henkel AG & Co. KGaA, Duesseldorf (DE)

(72) Inventors: Phillip Jaiser, Langenfeld (DE); Torsten Lechner, Langenfeld (DE); Marc Nowottny, Moenchengladbach (DE); Carsten Mathiaszyk, Essen (DE); Juergen Schoepgens, Schwalmtal (DE); Andreas Walter, Ratingen (DE); Carolin Kruppa, Hilden (DE); Avni Tairi, Duisburg (DE)

(73) Assignee: Henkel AG & Co. KGaA, Düsseldorf (DE)

( * ) Notice: Subject to any disclaimer, the term of this patent is extended or adjusted under 35 U.S.C. 154(b) by 222 days.

(21) Appl. No.: 18/273,047

(22) PCT Filed: Jan. 12, 2022

(86) PCT No.: PCT/EP2022/050556
§ 371 (c)(1),
(2) Date: Jul. 19, 2023

(87) PCT Pub. No.: WO2022/167184
PCT Pub. Date: Aug. 11, 2022

(65) Prior Publication Data

US 2024/0108563 A1 Apr. 4, 2024

(30) Foreign Application Priority Data

Feb. 5, 2021 (DE) ........................ 10 2021 201 098

(51) Int. Cl.
*A61K 8/58* (2006.01)
*A61Q 5/06* (2006.01)

(52) U.S. Cl.
CPC .............. *A61K 8/585* (2013.01); *A61Q 5/065* (2013.01); *A61K 2800/591* (2013.01)

(58) Field of Classification Search
CPC .............. A61K 8/585; A61K 2800/591; A61K 2800/805; A61Q 5/065; A61Q 5/06
See application file for complete search history.

(56) References Cited

U.S. PATENT DOCUMENTS

| | | | |
|---|---|---|---|
| 2005/0130865 A1 | | 6/2005 | Schmid et al. |
| 2010/0083446 A1 | | 4/2010 | Brun et al. |
| 2022/0054394 A1 | | 2/2022 | Schoepgens et al. |
| 2022/0249345 A1 | | 8/2022 | Lechner et al. |
| 2022/0313582 A1 | | 10/2022 | Krohn et al. |

FOREIGN PATENT DOCUMENTS

| | | | | |
|---|---|---|---|---|
| DE | 19738866 | A1 | | 3/1999 |
| DE | 102018132893 | A | | 6/2020 |
| DE | 102019206914 | A1 | * | 11/2020 |
| DE | 102019207062 | A1 | * | 11/2020 |
| EP | 2168633 | A2 | | 3/2010 |
| JP | 2007-099693 | A | | 4/2007 |
| JP | 2014-532757 | A | | 12/2014 |
| WO | 2013/068979 | A2 | | 5/2013 |
| WO | WO2020126140 | A1 | * | 6/2020 |

OTHER PUBLICATIONS

Beari et al.: "Organofunctional alkoxysilanes in dilute aqueous solution: new accounts on the dynamic structural mutability", Journal of Organometallic Chemistry, 2001, pp. 208-216, vol. 625, Elsevier Science B.V.
Search Report dated May 10, 2022, of parallel PCT application No. PCT/EP2022/050556, 25 pages, for information purpose only.

* cited by examiner

*Primary Examiner* — Robert A Wax
*Assistant Examiner* — Kimberly Barber
(74) *Attorney, Agent, or Firm* — Blank Rome LLP

(57) ABSTRACT

A method may be used for treating keratin material, such as human hair, where a cosmetic agent is applied to the keratin material. After an exposure time, the cosmetic agent is rinsed off. The cosmetic agent may include a mixture of organic $C_1$-$C_6$ alkoxy siloxanes, said mixture being obtained by specifically hydrolyzing and precondensing one or more organic $C_1$-$C_6$ alkoxy siloxanes by adding water and catalyst, and where the hydrolysis and precondensation is carried out in the absence of a solvent different from water.

18 Claims, No Drawings

METHOD FOR TREATING HUMAN HAIR WITH AGENTS CONTAINING MIXTURES OF ORGANIC $C_1$-$C_6$ ALKOXY SILOXANES

CROSS-REFERENCE TO RELATED APPLICATIONS

The present application is a national stage entry according to 35 U.S.C. § 371 of PCT application No.: PCT/EP2022/050556 filed on Jan. 12, 2022; which claims priority to German patent application 10 2021 201 098.9 filed on Feb. 5, 2021; all of which are incorporated herein by reference in their entirety and for all purposes.

TECHNICAL FIELD

The present application is in the field of cosmetics and relates to a method for treating human hair in which a cosmetic agent is applied to the hair and, after an exposure time, is rinsed off. The cosmetic agent is characterized in that it contains a mixture of organic $C_1$-$C_6$ alkoxy siloxanes, which mixture is obtained by specifically hydrolyzing and precondensing one or more organic $C_1$-$C_6$ alkoxy silanes by adding water and catalyst. The hydrolysis and precondensation is carried out here in the absence of a solvent different from water.

BACKGROUND

Changing the shape and color of keratinous fibers, in particular hair, represents an important area of modern cosmetics. To change the hair color, the skilled artisan is familiar with a variety of coloring system depending on the coloring requirements. Oxidation dyes are typically used for permanent, intense dyeing with good fastness properties and good gray coverage. Such coloring agents typically contain oxidation dye precursors, so-called developer components and coupler components, which together form the actual dyes under the influence of oxidizing agents, such as, for example, hydrogen peroxide. Oxidation dyes are characterized by very long-lasting color results.

When using direct dyes, dyes which are already formed diffuse out of the coloring agent into the hair fiber. In comparison with oxidative hair coloring, the colors obtained with direct dyes have a lower durability and a more rapid washing out. Colors with direct dyes usually remain on the hair for a period of between 5 and 20 hair washes.

The use of color pigments for brief changes in color on the hair and/or the skin is known. Color pigments are generally understood to mean insoluble dyeing substances. These are present undissolved in the form of small particles in the dyeing formulation and are only deposited from the outside onto the hair fibers and/or the skin surface. They can therefore generally be removed again without leaving residue by washing a few times with surfactant-containing cleaning agents. Various products of this type by the name of hair mascara are available on the market.

EP 2168633 B1 deals with the task of producing long-lasting hair coloring using pigments. The document teaches that, when using a combination of pigment, organosilicon compound, hydrophobic polymer and a solvent, colors can be produced on hair which are particularly resistant to shampoos.

The organic silicon compounds used in EP 2168633 B1 are reactive compounds from the class of alkoxy silanes. These alkoxy silanes hydrolyze at high speed in the presence of water and form—depending on the amounts used in each case of alkoxy silane and water—hydrolysis products and/or condensation products. The influence of the amount of water used in this reaction on the properties of the hydrolysis or condensation product is described, for example, in WO 2013068979 A2.

If these hydrolysis or condensation products are applied to keratin material, a film or a coating is formed on the keratin material, which completely surrounds the keratin material and in this way greatly influences the properties of the keratin material. Possible fields of application are, for example, permanent styling or else the permanent shape change of keratin fibers. In this case, the keratin fibers are mechanically brought into the desired shape and are then fixed in this form by forming the above-described coating. A further very particularly suitable application possibility is the coloring of keratin material; in the context of this application, the coating or the film is produced in the presence of a coloring compound, for example a pigment. The film colored by the pigment remains on the keratin material or the keratin fibers, and results in surprisingly washing-resistant colorations.

The great advantage of the coloring principle based on alkoxy silanes is that the high reactivity of this compound class enables very rapid coating. Thus, extremely good coloring results can be achieved even after very short application periods of only a few minutes. In addition to these advantages, however, the high reactivity of the alkoxy silanes also entails some disadvantages. Thus, even slight changes in the production and application conditions, such as the change in humidity and/or temperature, can lead to severe fluctuations in the product performance. In particular, the work leading to this invention has shown that the alkoxy silanes react extremely sensitively to the conditions that prevail during the preparation of the keratin treatment agents.

Analytical studies have shown that, in the production of various silane or siloxane mixtures and blends, complex hydrolysis and condensation reactions proceed, which lead to oligomeric products of different molecular size depending on the reaction conditions selected. In this context, it has been found that the molecular weight of these silane oligomers can have a great influence on the later product properties. If the wrong conditions are selected during the preparation, this can lead to the formation of excessively large or excessively small silane condensates, as a result of which the later product performance, in particular the later coloring capability on the keratin material, is adversely affected.

The object of the present application was to find an optimized method for the treatment of keratin material, in particular human hair. The mixtures of alkoxy siloxanes used in this method should be specifically prepared such that the optimal performance properties are achieved in a subsequent application. In particular, the agents produced in this way should have an improved coloring performance, i.e., in their application in a coloring method, colorings with higher color intensity and improved fastness properties, in particular with improved wash fastness and improved rubbing fastness, should be achieved. In addition, the mixtures of alkoxy siloxanes used in the hair treatment method should have improved storage stability.

SUMMARY

In the work leading to this invention, it has surprisingly been found that the aforementioned object can be achieved well if agents containing $C_1$-$C_6$ alkoxy siloxane mixtures are applied on human hair, wherein the $C_1$-$C_6$ alkoxy siloxane mixtures are produced on a specific hydrolytic path using a catalyst. In this context, it has been found to be particularly advantageous, when producing the mixture of organic $C_1$-$C_6$ alkoxy siloxanes, to dispense with the addition of solvents different from water. It was found that, by dispensing with the solvents different from water, such as ethanol, methanol, isopropanol, acetone, ethyl acetate, etc., a $C_1$-$C_6$ alkoxy siloxane mixture is obtained which has a greatly improved storage stability and also leads to more resistant films in the case of later application on the keratin material.

The organic $C_1$-$C_6$ alkoxy silanes used for the preparation are therefore admixed with a defined amount of water without prior mixing with an organic solvent in order to initiate a specific hydrolysis. Simultaneously with or shortly after the hydrolysis, a precondensation of the organic $C_1$-$C_6$ alkoxy silanes to the $C_1$-$C_6$ alkoxy siloxane mixtures follows. This $C_1$-$C_6$ alkoxy siloxane mixtures represent oligomeric compounds which, due to their partial hydrolysis or condensation, still have reactive groups and can react to the final polymer, film or coating during application on the human hair. Good coloring results with excellent fastness properties could be obtained particularly when the hydrolysis and condensation described above were initiated and accelerated by using a catalyst.

A first subject matter of the present invention is a method for treating keratin material, more particularly human hair, characterized in that a cosmetic agent is applied to the keratin material and, after an exposure time, is rinsed off, characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes by adding water and catalyst, and the hydrolysis and precondensation is carried out in the absence of a solvent different from water.

DETAILED DESCRIPTION

It has been found that the cosmetic agents, which contained the mixtures of organic $C_1$-$C_6$ alkoxy siloxanes produced in this specific manner, when used in a dyeing process resulted in very intense and uniform colorings having very good concealing power, rubbing fastness and wash fastness and had particularly good storage stability.

Keratin Material

Keratin material is understood to mean hair, skin, and nails (such as, for example, fingernails and/or toenails). Furthermore, wool, furs and feathers also fall under the definition of the keratin material.

Keratin material is preferably understood to be human hair, human skin and human nails, in particular fingernails and toenails. Keratin material is very particularly preferably understood to mean human hair.

Agent for Treating Keratin Material

Agents for treating keratin material are understood to mean, for example, agents for coloring keratin material, agents for reshaping or shaping keratin material, in particular keratin fibers, or else agents for the conditioning or for the care of the keratin material. The agents produced by the method according to the invention exhibit particularly good suitability for coloring keratin material, in particular for coloring keratin fibers, which are particularly preferably human hair.

In the context of this invention, the term “agent for coloring” is used for a coloring of the keratin material, in particular of hair, caused by use of coloring compounds, such as thermochromic and photochromic dyes, pigments, mica, direct dyes and/or oxidation dyes. In this dyeing, the aforementioned coloring compounds are deposited in a particularly homogeneous and smooth film on the surface of the keratin material or diffuse into the keratin fibers. The film forms in situ by the reaction or further reaction of the already precondensed $C_1$-$C_6$ alkoxy siloxanes, wherein the coloring compound(s) interact with this film or coating or are stored therein.

The cosmetic agent, which is applied to the keratin material, in particular human hair, and rinsed off, represents a ready-to-use agent according to the invention. This ready-to-use agent can, for example, be filled into a container and applied to the keratin material in this form without further dilution, mixing or other method steps. For reasons of storage stability, however, it has been found to be very particularly preferred for the ready-to-use cosmetic agent to be prepared by the hairdresser or user only shortly before use. For this preparation of the ready-to-use agent, the mixture of organic $C_1$-$C_6$ alkoxy siloxanes, which are made available in the form of a separately packaged concentrate, can, for example, be mixed with an aqueous cosmetic carrier formulation.

Furthermore, it is also possible to prepare the ready-to-use cosmetic agent by mixing three different preparations, wherein the first preparation contains the mixture of organic $C_1$-$C_6$ alkoxy siloxanes, the second preparation represents the water-containing carrier and the third preparation can contain further active or ingredients such as, for example, coloring substances, thickeners or acids and/or bases for setting the desired pH value.

Organic $C_1$-$C_6$ Alkoxy Siloxanes

Siloxanes are understood by a person skilled in the art to mean chemical compounds having the general formula $R_3Si—[O—SiR_2]_n—O—SiR_3$, wherein the functional groups R can independently be hydrogen atoms, alkyl groups or else substituted alkyl groups. In the case of siloxanes, the silicon atoms are each linked by an oxygen atom to their adjacent silicon atom: Si—O—Si. Siloxanes with $R{=}CH_3$ hot polydimethylsiloxanes. The index n indicates the degree of oligomerization or polymerization of the siloxane. Typically, the index n is at a number from 0 to 1000000, or from 0 to 100000 or from 0 to 10,000 or from 0 to 1000. At n equal to 0, the siloxane is present in the form of a dimer.

The organic $C_1$-$C_6$ alkoxy siloxanes of the present invention are characterized in that at least one functional group R is a $C_1$-$C_6$ alkoxy group. The $C_1$-$C_6$ alkoxy group bonded to the silicon atom represents a reactive leaving group which, when applied to the keratin material, enables further condensation or oligomerization or polymerization.

The organic $C_1$-$C_6$ alkoxy siloxanes are prepared by specifically hydrolyzing and precondensing one or more organic $C_1$-$C_6$ alkoxy silanes by adding water and catalyst, wherein in the reaction the addition of a solvent different from water is dispensed with.

Organic $C_1$-$C_6$ Alkoxy Silanes

The organic $C_1$-$C_6$ alkoxy silane(s) is/are organic, nonpolymeric silicon compounds, which are preferably selected from the group of silanes having one, two or three silicon atoms.

Organosilicon compounds, which are alternatively also referred to as organic silicon compounds, are compounds which either have a direct silicon-carbon bond (Si—C), or in which the carbon is linked to the silicon atom via an oxygen, nitrogen or sulfur atom. The organosilicon compounds according to the invention are preferably compounds which contain one to three silicon atoms. The organosilicon compounds particularly preferably contain one or two silicon atoms.

According to the IUPAC rules, the term silane represents a substance group of chemical compounds based on a silicon backbone and hydrogen. In the case of organic silanes, the hydrogen atoms are completely or partially replaced by organic groups such as (substituted) alkyl groups and/or alkoxy groups.

It is characteristic for the $C_1$-$C_6$ alkoxy silanes according to the invention that at least one $C_1$-$C_6$ alkoxy group is present directly bound to a silicon atom. The $C_1$-$C_6$ alkoxy silanes according to the invention thus comprise at least one structural unit R'R"R'"Si—O— ($C_1$-$C_6$ alkyl), wherein the functional groups R', R" and R'" represent the three other binding valences of the silicon atom.

The $C_1$-$C_6$ alkoxy group(s) bonded to the silicon atom are very reactive and are hydrolyzed at high speed in the presence of water, wherein the reaction rate inter alia also depends on the number of hydrolyzable groups per molecule. If the hydrolyzable $C_1$-$C_6$ alkoxy group is an ethoxy group, the organosilicon compound preferably contains a structural unit R'R"R'"Si—O—$CH_2$—$CH_3$. The functional groups R', R" and R'" in turn represent the three remaining free valences of the silicon atom.

In the context of a very particularly preferred embodiment, a cosmetic agent is used in the method according to the invention, which agent contains a mixture of $C_1$-$C_6$ alkoxy siloxanes, in the preparation of which one or more organic $C_1$-$C_6$ alkoxy silanes of formula (I) and/or (II) and/or (IV) are used.

In the context of a very particularly preferred embodiment, a method according to the invention is characterized in that the cosmetic agent contains a mixture of organic $C_1$-$C_6$ alkoxy siloxanes, which mixture is obtained by hydrolyzing and precondensing one or more organic $C_1$-$C_6$ alkoxy siloxanes of formula (I) and/or (II) and/or (IV)

$$R_1R_2N\text{-}L\text{-}Si(OR_3)_a(R_4)_b \quad (I)$$

where

- $R_1$, $R_2$ represent, independently of one another, a hydrogen atom or a $C_1$-$C_6$ alkyl group,
- L represents a linear or branched, divalent $C_1$-$C_{20}$ alkylene group,
- $R_3$, $R_4$ represent, independently of one another, a $C_1$-$C_6$ alkyl group,
- a represents an integer from 1 to 3, and
- b represents the integer 3-a, and $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

where

- $R_5$, $R_5'$, $R_5''$, $R_6$, $R_6'$ and $R_6''$ represent, independently of one another, a $C_1$-$C_6$ alkyl group,
- A, A', A", A'" and A"" represent, independently of one another, a linear or branched, divalent $C_1$-$C_{20}$ alkylene group,
- $R_7$ and $R_8$ represent, independently of one another, a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III), $$(A'''')\text{-}Si(R_6'')_{d''}(OR_5'')_{c''} \quad (III),$$

- c represents an integer from 1 to 3,
- d represents the integer 3−c,
- c' represents an integer from 1 to 3,
- d' represents the integer 3−c',
- c" represents an integer from 1 to 3,
- d" represents the integer 3−c',
- e represents 0 or 1,
- f represents 0 or 1,
- g represents 0 or 1, and
- h represents 0 or 1,
- with the proviso that at least one of the functional groups from e, f, g and h is different from 0, $$(R_9)_mSi(OR_{10})_k \quad (IV),$$

where

- $R_9$ represents a $C_1$-$C_{12}$ alkyl group or a $C_2$-$C_{12}$ alkenyl group,
- $R_{10}$ represents a $C_1$-$C_6$ alkyl group,
- k represents an integer from 1 to 4, and
- m represents the number 4−k.

Particularly preferred is the use of organic $C_1$-$C_6$ alkoxy silanes of formula (I) and/or of formula (II), $$R_1R_2N\text{-}L\text{-}Si(OR_3)_a(R_4)_b \quad (I)$$

where

- $R_1$, $R_2$ represent, independently of one another, a hydrogen atom or a $C_1$-$C_6$ alkyl group,
- L represents a linear or branched, divalent $C_1$-$C_{20}$ alkylene group,
- $R_3$, $R_4$ represent, independently of one another, a $C_1$-$C_6$ alkyl group,
- a represents an integer from 1 to 3, and
- b represents the integer 3-a, and $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

where

- R5, R5', R5", $R_6$, R6' and R6" represent, independently of one another, a $C_1$-$C_6$ alkyl group,
- A, A', A", A'" and A"" represent, independently of one another, a linear or branched, divalent $C_1$-$C_{20}$ alkylene group,
- $R_7$ and $R_8$ represent, independently of one another, a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III), $$(A'''')\text{-}Si(R_6'')_{d''}(OR_5'')_{c''} \quad (III),$$

- c represents an integer from 1 to 3,
- d represents the integer 3−c,
- c' represents an integer from 1 to 3,
- d' represents the integer 3−c',
- c" represents an integer from 1 to 3,
- d" represents the integer 3−c',
- e represents 0 or 1,
- f represents 0 or 1,
- g represents 0 or 1, and
- h represents 0 or 1,
- with the proviso that at least one of e, f, g and h is different from 0.

The substituents $R_1$, $R_2$, $R_3$, $R_4$, $R_5$, $R_5'$, $R_5''$, $R_6$, $R_6'$, $R_6''$, $R_7$, $R_8$, L, A, A', A", A'" and A"" in the compounds of formula (I) and (II) are explained by way of example below:

Examples of a $C_1$-$C_6$ alkyl group are the groups methyl, ethyl, propyl, isopropyl, n-butyl, s-butyl and t-butyl, n-pentyl and n-hexyl. Propyl, ethyl and methyl are preferred alkyl functional groups. Examples of a $C_2$-$C_6$ alkenyl group are vinyl, allyl, but-2-enyl, but-3-enyl and isobutenyl; preferred $C_2$-$C_6$ alkenyl functional groups are vinyl and allyl. Preferred examples of a hydroxy-$C_1$-$C_6$ alkyl group are a hydroxymethyl, a 2-hydroxyethyl, a 2-hydroxypropyl, a 3-hydroxypropyl, a 4-hydroxybutyl group, a 5-hydroxypentyl and a 6-hydroxyhexyl group; a 2-hydroxyethyl group is particularly preferred. Examples of an amino-$C_1$-$C_6$ alkyl group are the aminomethyl group, the 2-aminoethyl group, and the 3-aminopropyl group. The 2-aminoethyl group is particularly preferred. Examples of a linear divalent $C_1$-$C_{20}$ alkylene group are, for example, the methylene group ($—CH_2—$), the ethylene group ($—CH_2—CH_2—$), the propylene group ($—CH_2—CH_2—CH_2—$) and the butylene group ($CH_2—CH_2—CH_2—CH_2—$). The propylene group ($—CH_2—CH_2—CH_2—$) is particularly preferred. Starting at a chain length of 3 C atoms, divalent alkylene groups may also be branched. Examples of branched, divalent $C_3$-$C_{20}$ alkylene groups are ($—CH_2—CH(CH_3)—$) and ($—CH_2—CH(CH_3)—CH_2—$).

In the organosilicon compound of formula (I)

$$R_1R_2N\text{-}L\text{-}Si(OR_3)_a(R_4)_b \quad (I),$$

the functional groups $R_1$ and $R_2$ represent, independently of one another, a hydrogen atom or a $C_1$-$C_6$ alkyl group. Most preferably, the functional groups $R_1$ and $R_2$ both represent a hydrogen atom.

The structural unit or left -L, which represents a linear or branched divalent $C_1$-$C_{20}$ alkylene group, is located in middle part of the organosilicon compound. The divalent $C_1$-$C_{20}$ alkylene group can alternatively also be referred to as a divalent or bivalent $C_1$-$C_{20}$ alkylene group, which means that each -L- group can enter into two bonds.

Preferably, -L- is a linear, divalent $C_1$-$C_{20}$ alkylene group. More preferably, -L-represents a linear divalent $C_1$-$C_6$ alkylene group. Particularly preferably, -L- represents a methylene group ($—CH_2—$), an ethylene group ($—CH_2—CH_2—$), a propylene group ($—CH_2—CH_2—CH_2—$) or a butylene group ($—CH_2—CH_2—CH_2—CH_2—$). Most preferably, L represents a propylene group ($—CH_2—CH_2—CH_2—$).

The organosilicon compounds of formula (I) according to the invention $$R_1R_2N\text{-}L\text{-}Si(OR_3)_a(R_4)_b \quad (I),$$

each bear, on one end, the silicon-containing group $—Si(OR_3)_a(R_4)_b$.

In the terminal structural unit $—Si(OR_3)_a(R_4)_b$, the $R_3$ and $R_4$ functional groups are each independently a $C_1$-$C_6$ alkyl group, particularly preferably $R_3$ and $R_4$, independently of one another, represent a methyl group or an ethyl group.

In this case, a represents an integer from 1 to 3, and b represents the integer 3-a. If a represents the number 3, then b is equal to 0. If a represents the number 2, then b is equal to 1. If a represents the number 1, then b is equal to 2.

It was possible to produce a keratin treatment agent having particularly good properties when at least one organic $C_1$-$C_6$ alkoxy silane of formula (I) was mixed with water or brought to the reaction, in which the functional groups $R_3$, $R_4$, independently of one another, represent a methyl group or an ethyl group.

Furthermore, it was possible to obtain colorings having the best wash fastness when at least one organic $C_1$-$C_6$ alkoxy silane of formula (I) was reacted with water in which the functional group a represents the number 3. In this case, the functional group b represents the number 0.

In a further preferred embodiment, a method according to the invention is characterized in that the cosmetic agent contains a mixture of organic $C_1$-$C_6$ alkoxy siloxanes, which mixture is obtained by hydrolyzing and precondensing one or more organic $C_1$-$C_6$ alkoxy silanes of formula (I), wherein $R_3$ and $R_4$ represent, independently of one another, a methyl group or an ethyl group, and a represents the number 3, and b represents the number 0.

In a further preferred embodiment, a method according to the invention is characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes of formula (I) by adding water and catalyst, $$R_1R_2N\text{-}L\text{-}Si(OR_3)_a(R_4)_b \quad (I),$$

where $R_1$ and $R_2$ both represent a hydrogen atom, and

L represents a linear, divalent $C_1$-$C_6$ alkylene group, preferably a propylene group ($—CH_2—CH_2—CH_2—$) or an ethylene group ($—CH_2—CH_2—$), $R_3$ represents an ethyl group or a methyl group, $R_4$ represents a methyl group or an ethyl group, a represents the number 3, and b represents the number 0.

To achieve the object according to the invention, particularly well-suited organosilicon compounds of formula (I) are:

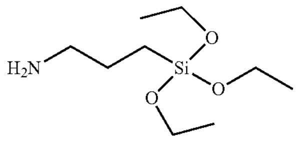

(3-aminopropyl)triethoxysilane

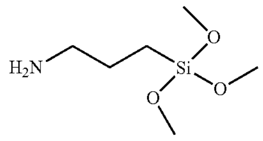

(3-aminopropyl)trimethoxysilane

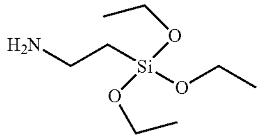

(2-aminoethyl)triethoxysilane

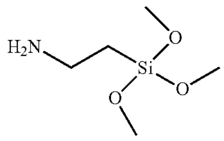

(2-aminoethyl)trimethoxysilane

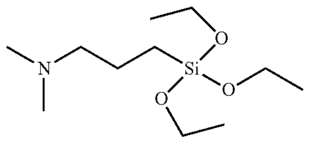

(3-dimethylaminopropyl)triethoxysilane

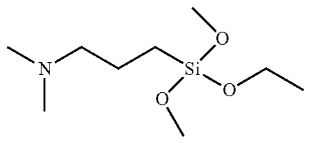

(3-dimethylaminopropyl)trimethoxysilane

-continued

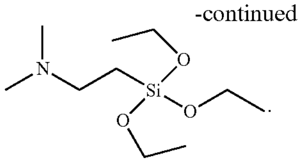

(2-dimethylaminoethyl)triethoxysilane

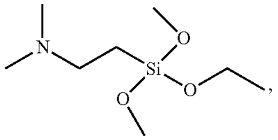

, and/or (2-dimethylaminoethyl)trimethoxysilane

In a further preferred embodiment, a method according to the invention is characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes selected from the group consisting of (3-aminopropyl)triethoxysilane
(3-aminopropyl)trimethoxysilane
1-(3-aminopropyl)silanetriol
(2-aminoethyl)triethoxysilane
(2-aminoethyl)trimethoxysilane
1-(2-aminoethyl)silanetriol
(3-dimethylaminopropyl)triethoxysilane
(3-dimethylaminopropyl)trimethoxysilane
1-(3-dimethylaminopropyl)silanetriol
(2-dimethylaminoethyl)triethoxysilane.
(2-dimethylaminoethyl)trimethoxysilane, and/or
1-(2-dimethylaminoethyl)silanetriol by adding water and catalyst.

The aforementioned organosilicon compounds of formula (I) are commercially available. (3-aminopropyl)trimethoxysilane can be purchased from Sigma-Aldrich, for example. (3-aminopropyl)triethoxysilane is commercially available from Sigma-Aldrich.

In a further preferred embodiment, a method according to the invention is characterized in that the cosmetic agent contains a mixture of organic $C_1$-$C_6$ alkoxy siloxanes, which mixture is obtained by mixing one or more organic $C_1$-$C_6$ alkoxy silanes of formula (II) with a solvent different from water and hydrolyzing and precondensing them by adding water and catalyst, $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad \text{(II).}$$

The organosilicon compounds of formula (II) according to the invention each bear the silicon-containing groups $(R_5O)_c(R_6)_dSi$— and —$Si(R_6')_{d'}(OR_5')_{c'}$ at their two ends.

The groups $(A)_e$-, —$[NR_7$-$(A')]_f$-, —$[O$-$(A'')]_g$- and —$[NR_8$-$(A''')]_h$- are in the middle part of the molecule of formula (II). In this case, each of the functional groups e, f, g and h can independently represent the number 0 or 1, with the proviso that at least one of the functional groups e, f, g and h is different from 0. In other words, an organosilicon compound of formula (II) according to the invention contains at least one grouping from the group consisting of -(A)-, —[$NR_7$-(A')]-, —[O-(A'')]- and —[$NR_8$-(A''')]-.

In the two terminal structural units $(R_5O)_c(R_6)_dSi$— and —$Si(R_6')_{d'}(OR_5')_{c'}$, the functional groups $R_5$, $R_5'$, $R_5''$ represent, independently of one another, a $C_1$-$C_6$ alkyl group. The functional groups $R_6$, $R_6'$ and $R_6''$ represent, independently of one another, a $C_1$-$C_6$ alkyl group.

In this case, c is an integer from 1 to 3, and d is the integer 3−c. If c represents the number 3, then d is equal to 0. If c represents the number 2, then d is equal to 1. If c represents the number 1, then d is equal to 2.

Similarly, c' represents an integer of 1 to 3, and d' represents the integer 3−c'. If c' represents the number 3, then d' is equal to 0. If c' represents the number 2, then d' is equal to 1. If c' represents the number 1, then d' is equal to 2.

Colors with the best wash fastness were obtained when the functional groups c and c' both represented the number 3. In this case, d and d' both represent the number 0.

In a further preferred embodiment, a method according to the invention is characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes of formula (II) by adding water and catalyst, $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad \text{(II),}$$

where $R_5$ and $R_5'$ represent, independently of each other, a methyl group or an ethyl group,
c and c' both represent the number 3, and
d and d' both represent the number 0.

If c and c' both represent the number 3 and d and d' both represent the number 0, the inventive organosilicon compound of formula (IIa) corresponds to:

$$(R_5O)_3Si\text{-}(A)_e\text{-}[NR_7\text{-}(A')]_f\text{-}[O\text{-}(A'')]_g\text{-}[NR_8\text{-}(A''')]_h\text{-}Si(OR_5')_3 \quad \text{(IIa).}$$

The functional groups e, f, g and h can independently represent the number 0 or 1, where at least one functional group of e, f, g and h is different from zero. The abbreviations e, f, g and h therefore define which of the groupings -$(A)_e$-, —$[NR_7$-$(A')]_f$-, —$[O$-$(A'')]_g$- and —$[NR_8$-$(A''')]_h$- are located in the middle part of the organosilicon compound of formula (II).

In this context, the presence of certain groupings has proven to be particularly advantageous with regard to achieving wash-fast color results. Particularly good results were obtained when at least two of the functional groups e, f, g and h represented the number 1. Most preferably, e and f both represent the number 1. Furthermore, g and h very particularly preferably both represent the number 0.

If e and f both represent the number 1, and g and h both represent the number 0, the organosilicon compound according to the invention corresponds to formula (IIb):

$$(R_5O)_c(R_6)_dSi\text{-}(A)\text{-}[NR_7\text{-}(A')]—Si(R_6')_{d'}(OR_5')_{c'} \quad \text{(IIb).}$$

The functional groups A, A', A'', A''' and A'''' represent, independently of one another, a linear or branched divalent $C_1$-$C_{20}$ alkylene group. A, A', A'', A''' and A'''' preferably represent, independently of one another, a linear or branched divalent $C_1$-$C_{20}$ alkylene group. More preferably, the functional groups A, A', A'', A''' and A'''' represent, independently of one another, a linear divalent $C_1$-$C_6$ alkylene group.

The divalent $C_1$-$C_{20}$ alkylene group can alternatively also be referred to as a divalent or bivalent $C_1$-$C_{20}$ alkylene group, which means that each grouping A, A', A'', A''' and A'''' can undergo two bonds.

Particularly preferably, the functional groups A, A', A'', A''' and A'''' represent, independently of one another, a methylene group (—$CH_2$—), an ethylene group (—$CH_2$—$CH_2$—), a propylene group (—$CH_2$—$CH_2$—$CH_2$—) or a butylene group (—$CH_2$—$CH_2$—$CH_2$—$CH_2$—). Very particularly preferably, the functional groups A, A', A'', A''' and A'' represent a propylene group ($—CH_2—CH_2—CH_2—$).

If the functional group f represents the number 1, the organosilicon compound of formula (II) according to the invention contains a structural grouping $—[NR_7\text{-}(A')]\text{-}$.

If the functional group h represents the number 1, the organosilicon compound of formula (II) according to the invention contains a structural group $—[NR_8\text{-}(A''')]\text{-}$.

In this context, $R_7$ and $R_8$ represent, independently of one another, a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group or a group of formula (III):

$$\text{-}(A'''')\text{-}Si(R_6'')_{d''}(OR_5'')_{c''} \quad \text{(III)},$$

Most preferably, the functional groups $R_7$ and $R_8$ represent, independently of one another, a hydrogen atom, a methyl group, a 2-hydroxyethyl group, a 2-alkenyl group, a 2-aminoethyl group or a grouping of formula (III).

If the functional group f represents the number 1 and the functional group h represents the number 0, the organosilicon compound according to the invention contains the grouping $[NR_7\text{-}(A')]$, but not the grouping $—[NR_8\text{-}(A''')]$ If the functional group $R_7$ represents a grouping of formula (III), the pretreatment agent (a) contains an organosilicon compound with 3 reactive silane groups.

In a further preferred embodiment, a method according to the invention is characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes of formula (II) by adding water and catalyst, $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad \text{(II)},$$

where e and f both represent the number 1, g and h both represent the number 0,

A and A' represent, independently of one another, a linear, divalent $C_1$-$C_6$ alkylene group and $R_7$ represents a hydrogen atom, a methyl group, a 2-hydroxyethyl group, a 2-alkenyl group, a 2-aminoethyl group or a grouping of formula (III).

In a further preferred embodiment, a method according to the invention is characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes of formula (II) by adding water and catalyst, where e and f both represent the number 1, g and h both represent the number 0, A and A' represent, independently of one another, a methylene group ($—CH_2—$), an ethylene group ($—CH_2—CH_2—$) or a propylene group ($—CH_2—CH_2—CH_2$), and $R_7$ represents a hydrogen atom, a methyl group, a 2-hydroxyethyl group, a 2-alkenyl group, a 2-aminoethyl group or a grouping of formula (III).

To achieve the object according to the invention, suitable organosilicon compounds of formula (II) are:

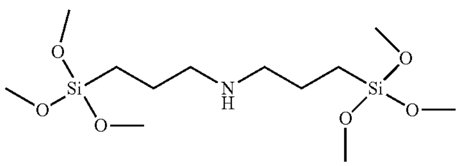

3-(trimethoxysilyl)-N-[3-(trimethoxysilyl)propyl]-1-propanamine

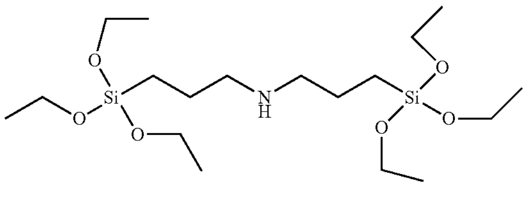

3-(triethoxysilyl)-N-[3-(triethoxysilyl)propyl]-1-propanamine

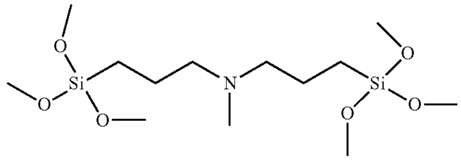

N-methyl-3-(trimethoxysilyl)-N-[3-(trimethoxysilyl)propyl]-1-propanamine

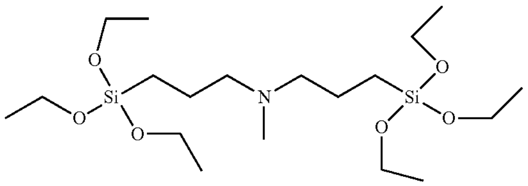

N-methyl-3-(triethoxysilyl)-N-[3-(triethoxysilyl)propyl]-1-propanamine

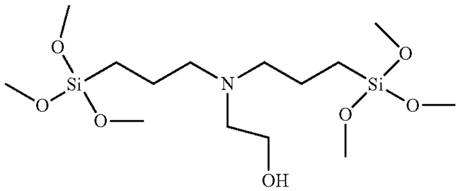

2-[bis[3-(trimethoxysilyl)propyl]amino]ethanol

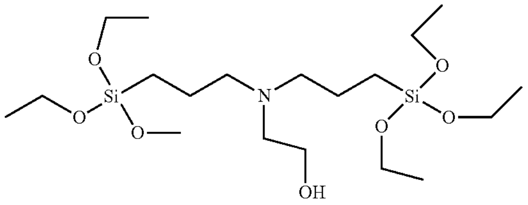

2-[bis[3-(triethoxysilyl)propyl]amino]ethanol

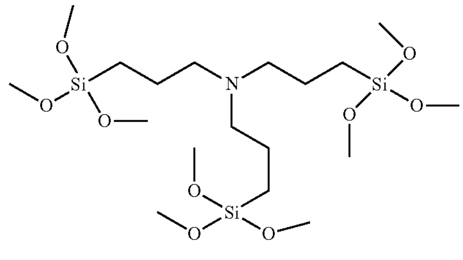

3-(trimethoxysilyl)-N,N-bis[3-(trimethoxysilyl)propyl]-1-propanamine

-continued

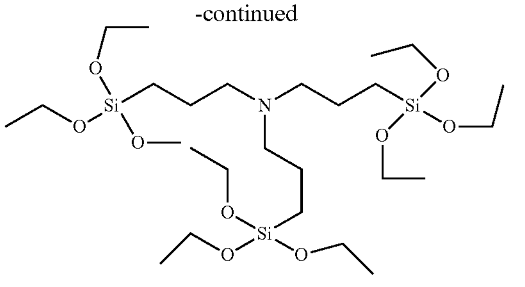

3-(triethoxysilyl)-N,N-bis[3-(triethoxysilyl)propyl]-1-propanamine

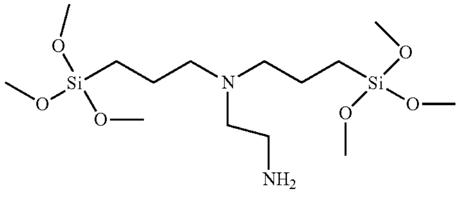

N1,N1-bis[3-(trimethoxysilyl)propyl]-1,2-ethanediamine

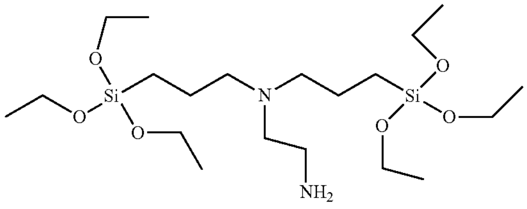

N1,N1-bis[3-(triethoxysilyl)propyl]-2-propen-1-amine

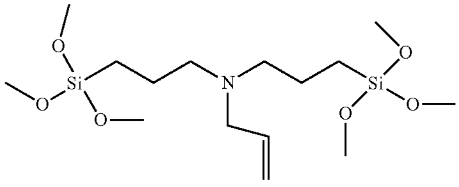

N,N-bis[3-(triethoxysilyl)propyl]-2-propen-1-amine

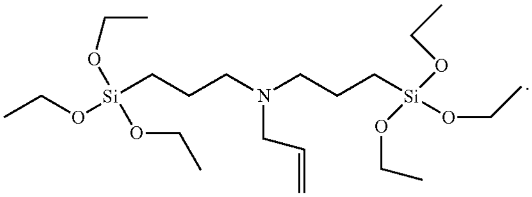

N,N-bis[3-(triethoxysilyl)propyl]-2-propen-1-amine

The aforementioned organosilicon compounds of formula (II) are commercially available.

Bis(trimethoxysilylpropyl)amine with the CAS number 82985-35-1 can, for example, be purchased from Sigma-Aldrich.

Bis[3-(triethoxysilyl)propyl]amines with the CAS number 13497-18-2 can be purchased from Sigma-Aldrich, for example.

N-methyl-3-(trimethoxysilyl)-N-[3-(trimethoxysilyppropyl]-1-propanamine is alternatively also referred to as bis (3-trimethoxysilylpropyl)-N-methylamine and can be purchased commercially from Sigma-Aldrich or Fluorochem.

3-(triethoxysilyl)-N,N-bis[3-(triethoxysilyl)propyl]-1-propanamine with the CAS number 18784-74-2 can be purchased, for example, from Fluorochem or Sigma-Aldrich.

In a further preferred embodiment, a method according to the invention is characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes selected from the group consisting of 3-(trimethoxysilyl)-N[3-(trimethoxysilyppropyl]-1-propanamine 3-(triethoxysilyl)-N[3-(triethoxysilyl)propyl]-1-propanamine N-methyl-3-(trimethoxysilyl)-N-[3-(trimethoxysilyppropyl]-1-propanamine N-methyl-3-(triethoxysilyl)-N-[3-(triethoxysilyppropyl]-1-propanamine 2-[bis[3-(trimethoxysilyl)propyl]amino]ethanol 2-[bis[3-(triethoxysilyl)propyl]amino]ethanol 3-(trimethoxysilyl)-N,N-bis[3-(trimethoxysilyl)propyl]-1-propanamine 3-(triethoxysilyl)-N,N-bis[3-(triethoxysilyl)propyl]-1-propanamine N1,N1-bis[3-(trimethoxysilyl)propyl]-1,2-ethanediamine N1,N1-bis[3-(triethoxysilyl)propyl]-1,2-ethanediamine N,N-bis[3-(trimethoxysilyppropyl]-2-propen-1-amine, and/or N,N-bis[3-(triethoxysilyppropyl]-2-propen-1-amine, by adding water and catalyst.

In further dyeing experiments, it has also been found to be very particularly advantageous if the cosmetic agent comprises a mixture of organic $C_1$-$C_6$ alkoxy siloxanes, which mixture is obtained by mixing one or more organic $C_1$-$C_6$ alkoxy silanes of formula (IV) with a solvent different from water and specifically hydrolyzing and precondensing them by adding water and catalyst $$(R_9)_m Si(OR_{10})_k \quad \text{(IV).}$$

The compounds of formula (IV) are organosilicon compounds selected from silanes having one, two or three silicon atoms, wherein the organosilicon compound comprises one or more hydrolyzable groups per molecule.

The organic silicon compound(s) of formula (IV) can be referred to as silanes of the type $C_1$-$C_{12}$-alkyl-$C_1$-$C_6$ alkoxy silanes (in the case of k=1 to 3) or as silanes of the type tetra-$C_1$-$C_6$ alkoxy silanes (in the case of k=4), $$(R_9)_m Si(OR_{10})_k \quad \text{(IV),}$$

where $R_9$ represents a $C_1$-$C_{12}$ alkyl group or a $C_2$-$C_{12}$ alkenyl group, $R_{10}$ represents a $C_1$-$C_6$ alkyl group, k represents an integer from 1 to 4, and m represents the integer 4−k.

In a further preferred embodiment, a method according to the invention is characterized in that the cosmetic agent contains a mixture of organic $C_1$-$C_6$ alkoxy siloxanes, which mixture is obtained by mixing one or more organic $C_1$-$C_6$ alkoxy silanes of formula (IV) with a solvent different from water and specifically hydrolyzing and precondensing them by adding water and catalyst, $$(R_9)_m Si(OR_{10})_k \quad \text{(IV),}$$

where $R_9$ represents a $C_1$-$C_{12}$ alkyl group or a $C_2$-$C_{12}$ alkenyl group, $R_{10}$ represents a $C_1$-$C_6$ alkyl group, k represents an integer from 1 to 4, and m represents the number 4−k.

In the organic $C_1$-$C_6$ alkoxy silanes of formula (IV), the functional group $R_9$ represents a $C_1$-$C_{12}$ alkyl group or a $C_2$-$C_{12}$ alkenyl group. This $C_1$-$C_{12}$ alkyl group is saturated and can be linear or branched. The $C_2$-$C_{12}$ alkenyl group is unsaturated, may comprise one or more double bonds and may be linear or branched. $R_9$ preferably represents a linear $C_1$-$C_8$ alkyl group. Preferably, $R_9$ represents a methyl group, an ethyl group, an n-propyl group, an n-butyl group, an n-pentyl group, an n-hexyl group, an n-octyl group or an n-dodecyl group. Particularly preferably, $R_9$ represents a methyl group, an ethyl group or an n-octyl group.

In the organosilicon compounds of formula (IV), the $R_{10}$ functional group represents a $C_1$-$C_6$ alkyl group. Particularly preferably, $R_{10}$ represents a methyl group or an ethyl group.

Moreover, k represents an integer from 1 to 4, and m represents the integer 4−k.

If k represents the number 4, m is equal to 0. In this case, the silanes of formula (IV) are tetra-$C_1$-$C_6$ alkoxy silanes. Suitable silanes of this type are tetraethoxysilane or tetramethoxysilane.

If k represents the number 3, m is equal to 1. In this case, the silanes of formula (IV) are $C_1$-$C_{12}$-alkyl-tri-$C_1$-$C_6$ alkoxy silanes.

If k represents the number 2, m is equal to 2. In this case, the silanes of formula (IV) are Di-$C_1$-$C_{12}$-alkyl-di-$C_1$-$C_6$ alkoxy silanes.

If k represents the number 1, m is equal to 3. In this case, the silanes of formula (IV) are tri-$C_1$-$C_{12}$ alkyl-$C_1$-$C_6$ alkoxy silanes.

It was possible to obtain colorings with the best wash-fastnesses when, during the establishment of the preparation according to the invention, at least one organosilicon compound of formula (IV) was used in which the functional group k represents the number 3. In this case, the functional group m represents the number 1.

Furthermore, particularly good results were obtained when, during the establishment of the preparation according to the invention, at least one organic silicon compound of formula (IV) is used, in which the functional group 9 represents a $C_1$-$C_8$ alkyl group, and the functional group $R_{10}$ represents a methyl group or an ethyl group.

In a further very particularly preferred embodiment, a method according to the invention is characterized in that the cosmetic agent comprises a mixture of organic $C_1$-$C_6$ alkoxy siloxanes, which mixture is obtained by specifically hydrolyzing and precondensing one or more organic $C_1$-$C_6$ alkoxy silanes of formula (IV) by adding water and catalyst, $$(R_9)_m Si(OR_{10})_k \quad (IV),$$

where $R_9$ represents a $C_1$-$C_8$ alkyl group, $R_{10}$ represents a methyl group or an ethyl group, k represents the number 3, and m represents the number 1.

To achieve the object according to the invention, particularly well-suited organosilicon compounds of formula (IV) are:

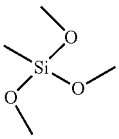

methyltrimethoxysilane

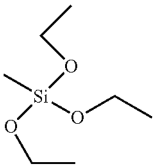

methyltriethoxysilane

-continued

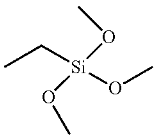

ethyltrimethoxysilane

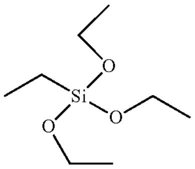

ethyltriethoxysilane

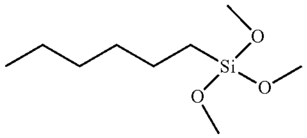

n-hexyltrimethoxysilane (also referred to as hexyltrimethoxysaline)

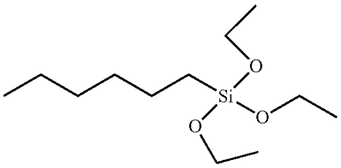

n-hexyltriethoxysilane (also referred to as hexyltriethoxysaline)

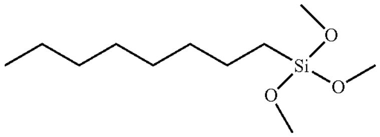

n-octyltrimethoxysilane (also referred to as octyltrimethoxysaline)

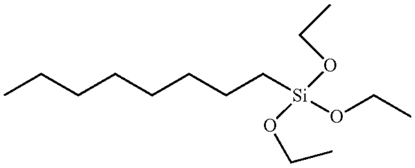

n-octyltriethoxysilane (also referred to as octyltriethoxysaline)

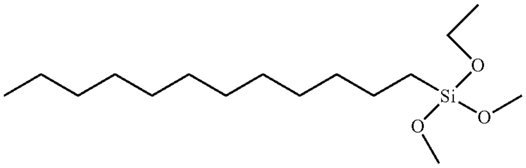

n-dodecyltrimethoxysilane (also referred to as dodecyltrimethoxysaline)

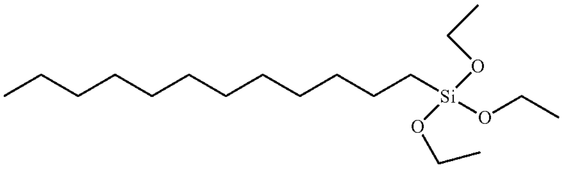

n-dodecyltriethoxysilane (also referred to as dodecyltriethoxysaline)

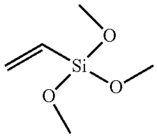

vinyltrimethoxysilane

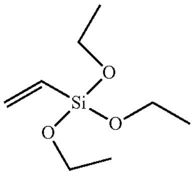

vinyltriethoxysilane

-continued

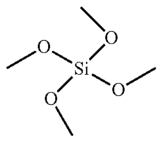

tetramethoxysilane

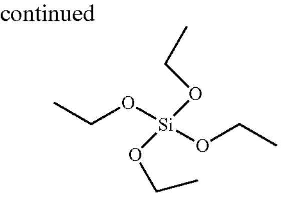

tetrylethoxysilane

In a further preferred embodiment, a method according to the invention is characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes selected from the group consisting of methyltrimethoxysilane
methyltriethoxysilane
ethyltrimethoxysilane
ethyltriethoxysilane
hexyltrimethoxysilane
hexyltriethoxysilane
octyltrimethoxysilane
octyltriethoxysilane
dodecyltrimethoxysilane, and/or
dodecyltriethoxysilane,
vinyltrimethoxysilane
vinyltriethoxysilane
tetramethoxysilane
tetraethoxysilane by adding water and catalyst.

In summary, a method according to the invention in a further preferred embodiment is characterized in that the cosmetic agent contains a mixture of organic $C_1$-$C_6$ alkoxy siloxanes which is obtained by one or more organic $C_1$-$C_6$ alkoxy silanes being hydrolyzed and precondensed that are selected from the group consisting of methyltrimethoxysilane
methyltriethoxysilane
ethyltrimethoxysilane
ethyltriethoxysilane
hexyltrimethoxysilane
hexyltriethoxysilane
octyltrimethoxysilane
octyltriethoxysilane
dodecyltrimethoxysilane,
dodecyltriethoxysilane,
vinyltrimethoxysilane
vinyltriethoxysilane
tetramethoxysilane
tetraethoxysilane
(3-aminopropyl)triethoxysilane
(3-aminopropyl)trimethoxysilane
(2-aminoethyl)triethoxysilane
(2-aminoethyl)trimethoxysilane
(3-dimethylaminopropyl)triethoxysilane
(3-dimethylaminopropyl)trimethoxysilane
(2-dimethylaminoethyl)triethoxysilane, and
(2-dimethylaminoethyl)trimethoxysilane.

When producing the mixture from $C_1$-$C_6$ alkoxy siloxanes, only an organic $C_1$-$C_6$ alkoxy silane from the group of the compounds of formula (I), only an organic $C_1$-$C_6$ alkoxy silane from the group of the compounds of formula (II), or else only an organic $C_1$-$C_6$ alkoxy silane from the group of the compounds of formula (IV) can be used.

Cosmetic agents having particularly advantageous properties were, however, obtained when, during the preparation of the mixture of $C_1$-$C_6$ alkoxy siloxanes, also mixtures of different $C_1$-$C_6$ alkoxy silanes were used. Particularly good results were obtained when both at least one organic $C_1$-$C_6$ alkoxy silane of formula (I), and also at least one organic $C_1$-$C_6$ alkoxy silane of formula (IV). When used on the keratin material, corresponding agents resulted in the formation of particularly flexible and resistant coatings or films.

In this context, it was of particular advantage to use the organic $C_1$-$C_6$ alkoxy silane(s) of formula (I) and the organic $C_1$-$C_6$ alkoxy silane(s) of formula (IV) in specific quantity ratios.

In a further particularly preferred embodiment, a method according to the invention is characterized in that the cosmetic agent comprises a mixture of organic $C_1$-$C_6$ alkoxy siloxanes, which mixture is obtained by using one or more organic $C_1$-$C_6$ alkoxy silanes of formula (I) and one or more organic $C_1$-$C_6$ alkoxy silanes of formula (IV) in a weight ratio of (I)/(IV) from 1:1 to 1:10, preferably from 1:1 to 1:8, more preferably from 1:1 to 1:6, even more preferably from 1:1 to 1:4 and very particularly preferably from 1:2 to 1:4.

At a weight ratio of the organic $C_1$-$C_6$ alkoxy silanes of formula (I) and of organic $C_1$-$C_6$ alkoxy silanes of formula (IV), i.e., at a weight ratio (I)/(IV) of 1:1, it is possible, for example, to use 1 part by weight of (3-aminopropyl) triethoxysilane and 1 part by weight of methyltriethoxysilane. Furthermore, it is also possible to use 1 part by weight of (3-aminopropyl) triethoxysilane and 1 part by weight of methyltrimethoxysilane.

At a weight ratio of the organic $C_1$-$C_6$ alkoxy silanes of formula (I) and of organic $C_1$-$C_6$ alkoxy silanes of formula (IV), i.e., at a weight ratio (I)/(IV) of 1:10, it is possible to use, for example, 1 part by weight of (3-aminopropyl) triethoxysilane and 10 parts by weight of methyltriethoxysilane. Furthermore, it is also possible to use 1 part by weight of (3-aminopropyl) triethoxysilane and 10 parts by weight of methyltrimethoxysilane.

The indicated weight ratios are understood to include the total amount of all organic $C_1$-$C_6$ alkoxy silanes of formula (I) used in the preparation of the mixture of organic $C_1$-$C_6$ alkoxy siloxanes, which is set in relation to the total amount of all organic $C_1$-$C_6$ alkoxy silanes of formula (IV).

The weight ratio of (I)/(IV) is very particularly preferably from 1:1 to 1:8, more preferably from 1:1 to 1:6, even more preferably from 1:1 to 1:4 and very particularly preferably from 1:2 to 1:4.

In other words, it has proven to be very particularly preferred if the organic $C_1$-$C_6$ alkoxy silanes of formula (IV), compared to organic $C_1$-$C_6$ alkoxy silanes of formula (I), are used in a two- to four-fold excess of weight.

Furthermore, good results were also obtained when both at least one organic $C_1$-$C_6$ alkoxy silane of formula (I), and also at least one organic $C_1$-$C_6$ alkoxy silane of formula (II) were used. In this context, it was advantageous to use $C_1$-$C_6$ alkoxy silanes of formula (I) and the organic $C_1$-$C_6$ alkoxy silane of formula (II) in certain quantitative ratios.

In a further embodiment, a method according to the invention is characterized in that the cosmetic agent contains a mixture of organic $C_1$-$C_6$ alkoxy siloxanes, which mixture is obtained by using one or more organic $C_1$-$C_6$ alkoxy silanes of formula (I) and one or more organic $C_1$-$C_6$ alkoxy silanes of formula (II) in a weight ratio of (I)/(11) from 1:1 to 1:10, preferably from 1:1 to 1:8, more preferably from 1:1 to 1:6, even more preferably from 1:1 to 1:4 and very particularly preferably from 1:2 to 1:4.

Reaction Vessels

The preparation of the mixture of organic $C_1$-$C_6$ alkoxy siloxanes preferably take place in a reactor or reaction vessel suited for this purpose. A reaction vessel which is very well suited for smaller batches is, for example, a glass flask having a capacity of 1 liter, 3 liters or 5 liters, typically used for chemical reactions, for example a 3-liter single-neck or multi-neck flask with ground joints.

A delimited space (container, vessel) which has been specially designed and manufactured to allow for and be able to control a processing of reactions determined therein under defined conditions is referred to as a reactor.

For larger batches, it has been found to be advantageous to carry out the reaction in reactors made of metal. Typical reactors can comprise, for example, a filling quantity of 10 liters, 20 liters or 50 liters. Larger reactors for production scale can also comprise filling quantities of 100 liters, 500 liters or 1000 liters.

Double-wall reactors have two reactor shells or reactor walls, wherein a temperature control liquid can circulate in the region located between the two walls. This enables a particularly good setting of the temperature to the required values.

The use of reactors, in particular double wall reactors with an increased heat exchange surface, has also proven to be particularly suitable, wherein the heat exchange can take place either via internal fittings or else by using an external heat exchanger.

Corresponding reactors are, for example, laboratory reactors from IKA. In this context, the “LR-2.ST” models or the “magic plant” model can be mentioned.

Further reactors which can be used are reactors with thin-film evaporators, because a very good heat dissipation and thus a particularly exact temperature control can be carried out in this way. Thin-film evaporators are alternatively also referred to as thin-layer evaporators. Thin-film evaporators can be purchased commercially, for example, from Asahi Glassplant Inc.

Dispensing With Solvent

As already described above, the mixture of organic $C_1$-$C_6$ alkoxy siloxanes is prepared by hydrolysis and precondensation of one or more organic $C_1$-$C_6$ alkoxy silanes by adding a defined amount of water and catalyst.

The hydrolysis and precondensation takes place in the absence of a solvent different from water, which means that, although water is mixed with the organic $C_1$-$C_6$ alkoxy silanes for the hydrolysis and precondensation, no further solvent beyond that is added to this reaction mixture.

Solvents which are dispensed with are, for example, ethanol, methanol, isopropanol, tetrahydrofuran, dichloromethane, acetone, ethyl acetate and acetonitrile. It has proven to be particularly advantageous if the method according to the invention is carried out without addition of a solvent from the group consisting of methanol, ethanol, isopropanol and acetone.

In the context of a further preferred embodiment, a method according to the invention is therefore characterized in that the hydrolysis and precondensation is carried out in the absence of a solvent from the group consisting of methanol, ethanol, isopropanol, n-propanol, n-pentanol, n-hexanol, benzyl alcohol, 2-phenylethanol, 1,2-propanediol, 1,3-propanediol, glycerol, acetone, tetrahydrofuran, dichloromethane, ethyl acetate and acetonitrile.

The absence of a solvent different from water is understood to mean that no solvent is added to the mixture of water and organic $C_1$-$C_6$. In the hydrolysis or condensation of the organic $C_1$-$C_6$ alkoxy silanes are naturally $C_1$-$C_6$ alkoxy groups, which react further in the presence of the water to the corresponding alcohol. If, for example, a methoxysilane (for example methyltrimethoxysilane) is used in the reaction, a small amount of methanol is present in the catalyzed hydrolysis or condensation. If an ethoxysilane (e.g., metyltriethoxysilane) is used in the reaction, ethanol is thus formed in an analogous manner in the reaction mixture. These small amounts of alcohols present due to the splitting off of the leaving groups are not added from the outside, but form in the meantime in the reaction mixture due to the reaction. However, these intermediate alcohol amounts are explicitly not to be understood as the solvent that is present within the meaning of the present invention. It is essential for the subject matter of the present application that no additional solvent such as methanol, ethanol, isopropanol, etc. is added from outside to the reaction mixture consisting of $C_1$-$C_6$ alkoxy silanes, water and catalyst (which is not a solvent).

In other words, a first subject matter of the present invention is a method for treating keratin material, in particular human hair, wherein a cosmetic agent is applied to the keratin material and, after an exposure time, rinsed off, characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes by adding water and catalyst, wherein the hydrolysis and precondensation is carried out without addition of a solvent different from water.

The addition of the solvent in this context is understood to mean adding the solvent to the mixture of $C_1$-$C_6$ alkoxy silanes, water and catalyst.

A method for treating keratin material, in particular human hair, is preferred, wherein a cosmetic agent is applied to the keratin material and, after an exposure time, is rinsed off, characterized in that the cosmetic agent contains a mixture of organic $C_1$-$C_6$ alkoxy siloxanes, which mixture is obtained by specifically hydrolyzing and precondensing one or more organic $C_1$-$C_6$ alkoxy silanes by adding water and catalyst, wherein the hydrolysis and precondensation is carried out without addition of a solvent from the group consisting of methanol, ethanol, isopropanol, n-propanol, n-pentanol, n-hexanol, benzyl alcohol, 2-phenylethanol, 1,2-propanediol, 1,3-propanediol, glycerol, acetone, tetrahydrofuran, dichloromethane, ethyl acetate and acetonitrile.

After preparation of the mixture of organic $C_1$-$C_6$ alkoxy siloxanes, it has been found to be particularly preferred to remove the $C_1$-$C_6$ alcohols which are produced intermediately via the hydrolysis reaction. The removal can be effected by distillation under reduced pressure, for example using a rotary evaporator.

Specific Hydrolysis by Adding Water

The mixture of one or more organic $C_1$-$C_6$ alkoxy silanes, preferably those of formulae (I), (II) and/or (IV), are mixed or admixed with water in order to initiate a specific hydrolysis and thus a precondensation.

Water can be added, for example, by dropping or pouring the water into the organic $C_1$-$C_6$ alkoxy silanes.

In this case, the dripping or the addition of the water can take place at room temperature. However, it is particularly advantageous for the performance properties of the later cosmetic agent if the organic $C_1$-$C_6$ alkoxy silane(s) are heated to a temperature from 30 to 80° C., preferably from 35 to 75° C., more preferably from 40 to 70° C. and most preferably from 45 to 65° C. before water and catalyst are added.

In a further particularly preferred embodiment, a method according to the invention is characterized in that the organic $C_1$-$C_6$ alkoxy silane(s) are heated to a temperature from 30 to 80° C., preferably from 35 to 75° C., more preferably from 40 to 70° C. and most preferably from 45 to 65° C. before water and catalyst are added.

The preferred and particularly preferred temperature ranges can be adjusted by tempering the reaction vessel or reactor. For example, the reaction vessel or the reactor can be surrounded from the outside with a temperature-control bath, which can be, for example, a water bath or a silicone oil bath.

If the reaction is carried out in a double-wall reactor, a temperature-controlled liquid can also be passed through the space which is formed by the two walls and which surrounds the reaction chamber.

Since the hydrolysis reaction is exothermic, it has been found to be particularly advantageous to stir or mix the reaction mixture for improved heat dissipation. Particularly preferably, the water is therefore added while stirring. The reaction which is now initiated by addition of water and catalyst proceeds further exothermically, so that the reaction mixture remains at the preferred temperature ranges specified above or can even further heat up without further energy supply. It is preferred when the additional heating caused by the exothermicity of the reaction remains within a range of 5 to 20° C. If the reaction mixture heats up over this range, it is advantageous to cool the mixture.

The water can be added continuously, in portions or directly as the total amount. In order to ensure sufficient temperature control, the reaction mixture is adapted the addition quantity and speed of the water. Depending on the amount of silanes used, the addition and reaction can take place over a period of 2 minutes up to 72 hours.

The addition of the water initiates specific hydrolysis of the organic $C_1$-$C_6$ alkoxy silanes. Within the meaning of the present invention, a specific hydrolysis is understood to mean that a part, but not all, of the $C_1$-$C_6$ alkoxy groups present in the organic $C_1$-$C_6$ alkoxy silanes are hydrolyzed.

Particularly preferably, the specific hydrolysis is effected by addition of a substoichiometric amount of water. In this case, the amount of water used is below the amount that would theoretically be required to hydrolyze all existing hydrolyzable $C_1$-$C_6$ alkoxy groups on the Si atoms, i.e., the alkoxy silane groups. Very particular preference is therefore given to the partial hydrolysis of the organic $C_1$-$C_6$ alkoxy silanes.

The stoichiometric ratio of water to the organic $C_1$-$C_6$ alkoxy silanes can be defined by the proportion of molar equivalents of water (S–W), said water being calculated according to the following formula:

$$S-W = \frac{\text{mol(water)}}{\text{mol(silanes)} \times n(\text{alkoxy})}$$

where

S–W=molar equivalent of water mol(water)=molar amount of water used mol(silanes)=total molar amount of the $C_1$-$C_6$ alkoxy silanes used in the reaction n(alkoxy)=number of $C_1$-$C_6$ alkoxy groups per $C_1$-$C_6$ alkoxy silane In other words, the molar ratio of water gives the molar ratio of the molar amount of water used to the total number of moles of hydrolyzable $C_1$-$C_6$ alkoxy groups which are on the $C_1$-$C_6$ alkoxy silanes used.

In a further very particularly preferred embodiment, a method according to the invention is characterized in that the organic $C_1$-$C_6$ alkoxy silane(s) by addition of 0.10 to 0.80 molar equivalents of water (S–W), preferably 0.15 to 0.70, further preferably 0.20 to 0.60 and very particularly preferably 0.25 to 0.50 molar equivalents of water, the molar equivalents of water being calculated according to the formula $$S-W = \frac{\text{mol(water)}}{\text{mol(silanes)} \times n(\text{alkoxy})}$$

where

S–W=molar equivalent of water mol(water)=molar amount of water used mol(silanes)=total molar amount of the $C_1$-$C_6$ alkoxy silanes used in the reaction n(alkoxy)=number of $C_1$-$C_6$ alkoxy groups per $C_1$-$C_6$ alkoxy silane.

If the mixture of organic $C_1$-$C_6$ alkoxy siloxanes is prepared by the catalyzed specific hydrolysis of a $C_1$-$C_6$ alkoxy silane, the number of $C_1$-$C_6$ alkoxy groups per $C_1$-$C_6$ alkoxy silane corresponds to the number of $C_1$-$C_6$ alkoxy groups that are present in the silane of this structure. However, if a mixture of structurally different $C_1$-$C_6$ alkoxy silanes is used in the hydrolysis, then n(alkoxy) corresponds to the numerical average of $C_1$-$C_6$ alkoxy groups of the $C_1$-$C_6$ alkoxy silanes. Using the formula S–W, the molar equivalents of water are then calculated, for example, as follows:

$$S-W = \frac{\text{mol(water)}}{[\text{mol(silane } (I)) \times n(\text{alkoxy}(I))] + [\text{mol(silane } (IV)) \times n(\text{alkoxy}(IV))]}$$

where

S–W=molar equivalent of water mol(water)=molar amount of water used mol(silane (I))=total molar amount used of $C_1$-$C_6$ alkoxy silanes of formula (I)

n(alkoxy (I))=number of $C_1$-$C_6$ alkoxy groups per $C_1$-$C_6$ alkoxy silane of formula (I)

mol(silane (IV))=total molar amount used $C_1$-$C_6$ alkoxy silanes of formula (IV)

n(alkoxy (IV))=number of $C_1$-$C_6$ alkoxy groups per $C_1$-$C_6$ alkoxy silane of formula (IV)

EXAMPLE

In a reaction vessel, 20.0 g of 3-aminopropyltriethanesilane ($C_9H_{23}NO_3Si$=221.37 g/mol) and 50.0 g of methyltrimethoxysilane ($C_4H_{12}O_3Si$=136.22 g/mol) were mixed together.

20.0 g 3-aminopropyltriethanesilane=0.0903 mol (3 hydrolyzable alkoxy groups per molecule)

50.0 g methyltrimethoxysilane=0.367 mol (3 hydrolyzable alkoxy groups per molecule)

Subsequently, 10.0 g of water provided with catalyst (18.015 g/mol) were added dropwise while stirring.

10.0 g of water=0.555 mol

Molar equivalent water=0.555 mol/[(3×0.090 mol)+(3×0.367 mol)]=0.40

In this reaction, the $C_1$-$C_6$ alkoxy silanes were converted with 0.40 molar equivalents of water.

If further or other mixtures of $C_1$-$C_6$ alkoxy silanes are used, the formula S−W is adapted accordingly.

The reaction of the organic $C_1$-$C_6$ alkoxy silanes with water can take place in various ways. The reaction starts as soon as the $C_1$-$C_6$ alkoxy silanes come into contact with water by mixing. Once $C_1$-$C_6$ alkoxy silanes and water are in contact, an exothermic hydrolysis reaction takes place according to the following scheme (reaction scheme using the example of 3-aminopropyltriethoxy silane):

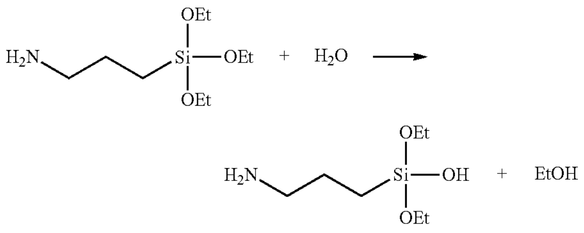

Depending on the number of hydrolyzable $C_1$-$C_6$ alkoxy groups per silane molecule, the hydrolysis reaction can also occur several times per $C_1$-$C_6$ alkoxy silane used:

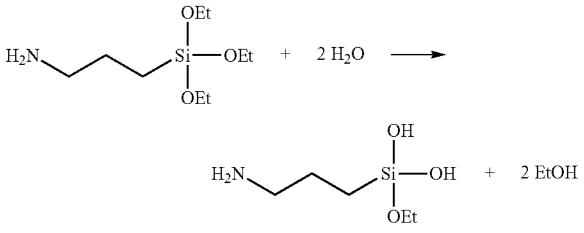

or

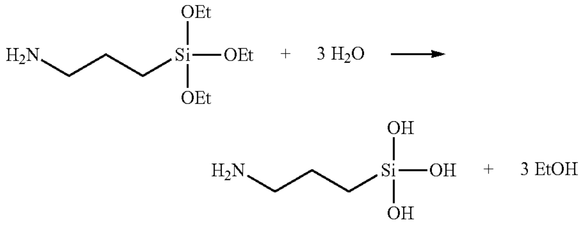

Hydrolysis using the example of methyltrimethoxysilane:

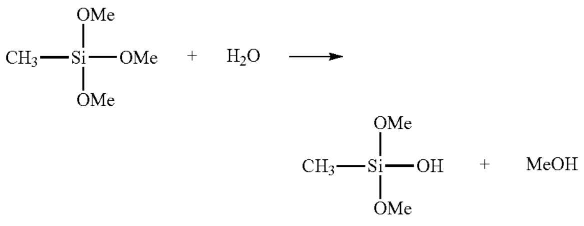

Depending on the amount of water used, the hydrolysis reaction can also be repeated several times per $C_1$-$C_6$ alkoxy silane used:

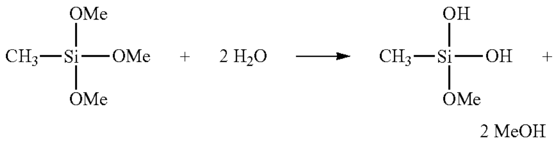

or

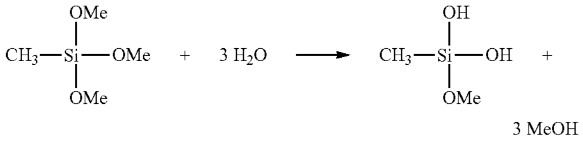

Precondensation

Condensation of the partially (or in parts completely) hydrolyzed $C_1$-$C_6$ alkoxy silanes takes place after hydrolysis, or almost simultaneously with hydrolysis. The precondensation can proceed, for example, according to the following scheme:

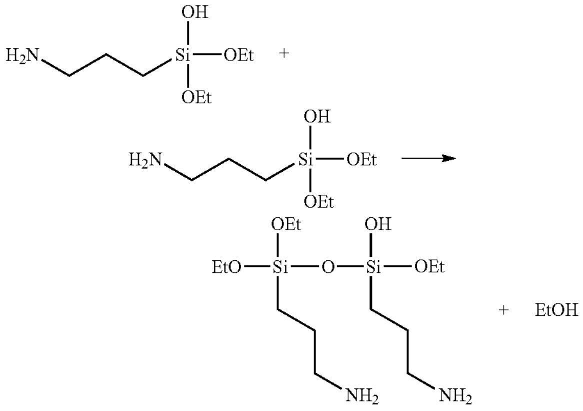

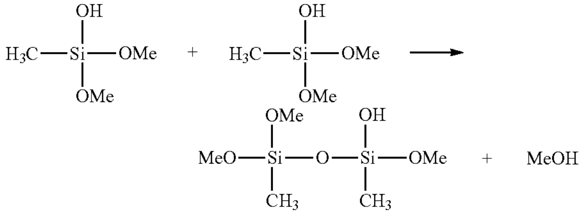

Both partially hydrolyzed and fully hydrolyzed $C_1$-$C_6$ alkoxy silanes can participate in the condensation reaction, undergoing condensation with not yet reacted, partially hydrolyzed or also fully hydrolyzed $C_1$-$C_6$ alkoxy silanes.

Possible condensation reactions are, for example (shown using the mixture (3-aminopropyl)triethoxysilane and methyltrimethoxysilane):

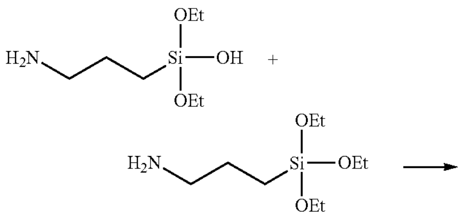

-continued

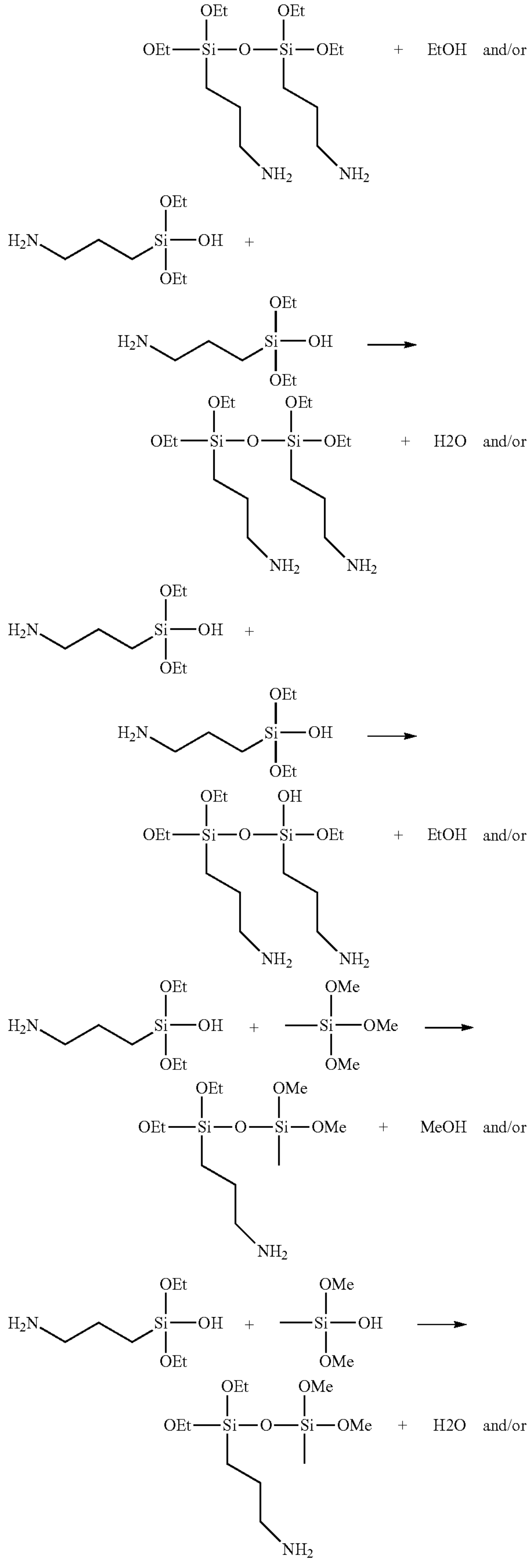

-continued

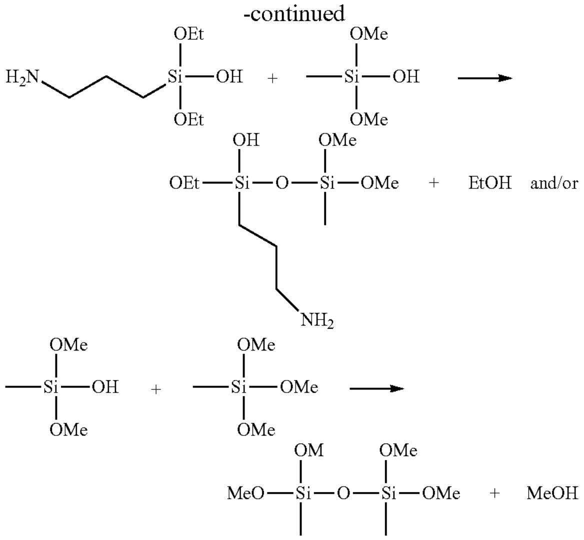

In the above exemplary reaction schemes, the condensation to form a dimer is shown, but further condensations to oligomers with a plurality of silane atoms are also possible and preferred.

Within the meaning of this invention, a precondensation is therefore the condensation of the organic $C_1$-$C_6$ alkoxy silanes to at least one dimer.

In other words, the first subject matter of the present invention is a method for treating keratin material, in particular human hair, wherein a cosmetic agent is applied to the keratin material and, after an exposure time, is rinsed off, characterized in that the cosmetic agent contains a mixture of organic $C_1$-$C_6$ alkoxy siloxanes, which mixture is obtained by hydrolyzing and precondensing one or more organic $C_1$-$C_6$ alkoxy silanes by adding water, preferably by adding a substoichiometric amount of water, and catalyst, wherein the hydrolysis and precondensation is carried out in the absence of a solvent different from water or without adding a solvent different from water.

In simplified terms, the first subject matter of the present invention is a method for treating keratin material, in particular human hair, wherein a cosmetic agent is applied to the keratin material and, after an exposure time, is rinsed off, characterized in that the cosmetic agent contains a mixture of organic $C_1$-$C_6$ alkoxy siloxanes, which mixture is obtained by mixing one or more organic $C_1$-$C_6$ alkoxy silanes with water, preferably a substoichiometric amount of water, and catalyst and brought to reaction.

Both partially hydrolyzed and fully hydrolyzed $C_1$-$C_6$ alkoxy silanes of the formula (I), for example, can participate in these condensation reactions and run through a condensation with still unreacted, partially or also fully hydrolyzed $C_1$-$C_6$ alkoxy silanes of the formula (I). In this case, the $C_1$-$C_6$ alkoxy silanes of formula (I) react with themselves.

Furthermore, both partially hydrolyzed and fully hydrolyzed $C_1$-$C_6$ alkoxy silanes of formula (I) can also be added to the condensation reactions which have a condensation with not yet reacted, partially hydrolyzed or else completely hydrolyzed $C_1$-$C_{12}$ alkyl $C_1$-$C_6$ alkoxy silanes of formula (IV). In this case, the $C_1$-$C_6$ alkoxy silanes of formula (I) react with the $C_1$-$C_6$ alkoxy silanes of formula (IV).

Moreover, both partially hydrolyzed and fully hydrolyzed $C_1$-$C_6$ alkoxy silanes of formula (IV) can participate in the condensation reactions and undergo a condensation with not yet reacted, partially or also fully hydrolyzed $C_1$-$C_6$ alkoxy silanes of formula (IV). In this case, the $C_1$-$C_6$ alkoxy silanes of formula (IV) react with themselves.

In the above exemplary reaction scheme, the condensation to form a dimer is shown, but the condensation to form oligomers having a plurality of silane atoms is also possible and also preferred.

The extent of the condensation reaction is determined by the amount of water added. The amount of water is preferably measured such that the precondensation is a partial condensation, "partial condensation" in this context meaning that not all condensable groups of the supplied silanes react with one another, so that the resulting organic silicon compound in each case has at least one hydrolyzable/condensable group per molecule in the agent.

Catalyst

In the preparation of the organic $C_1$-$C_6$ alkoxy siloxanes, the organic $C_1$-$C_6$ alkoxy silanes are specifically hydrolyzed and precondensed by adding water and catalyst. The addition of the catalyst brings about an initiation or acceleration of the hydrolysis reaction.

A catalyst is understood to mean a substance which increases the reaction rate by reducing the activation energy of a chemical reaction without being consumed itself. The catalyst can be added before, after or during the addition of the water.

For the preparation of the mixtures of organic $C_1$-$C_6$ alkoxy siloxanes, it has proven particularly advantageous to use a catalyst which dissolves or disperses in water, and then add it together with the water as a solution or dispersion to the mixture of organic $C_1$-$C_6$ alkoxy silanes and solvent.

Most preferably, the catalyst is selected from the group of the inorganic or organic acids and the inorganic or organic bases.

Particularly well-suited catalysts are inorganic and organic acids, which can preferably be selected from the group consisting of sulphuric acid, hydrochloric acid, phosphoric acid, maleic acid, citric acid, tartaric acid, malic acid, lactic acid, acetic acid, methanesulphonic acid, benzoic acid, malonic acid, oxalic acid and 1-hydroxyethane-1,1-diphosphonic acid. Sulfuric acid, hydrochloric acid and maleic acid are explicitly very particularly preferred.

In a further very particularly preferred embodiment, a method according to the invention is characterized in that the catalyst is selected from the group consisting of inorganic and organic acids, preferably from the group consisting of sulfuric acid, hydrochloric acid, phosphoric acid, maleic acid, citric acid, tartaric acid, malic acid, lactic acid, acetic acid, methanesulphonic acid, benzoic acid, malonic acid, oxalic acid and 1-hydroxyethane-1,1-diphosphonic acid.

Furthermore, particularly suitable catalysts are inorganic and organic bases, which can preferably be selected from the group consisting of sodium hydroxide, potassium hydroxide, magnesium hydroxide and calcium hydroxide. Sodium hydroxide and potassium hydroxide are very particularly preferred.

Furthermore, further inorganic alkalizing agents or bases can also be used. According to the invention, usable, inorganic alkalizing agents can preferably selected, for example, from the group, which is formed from sodium phosphate, potassium phosphate, sodium silicate, sodium metasilicate, potassium silicate, sodium carbonate and potassium carbonate.

In a further very particularly preferred embodiment, a method according to the invention is characterized in that the catalyst is selected from the group consisting of the inorganic and organic bases, preferably from the group consisting of sodium hydroxide, potassium hydroxide, magnesium hydroxide and calcium hydroxide.

Metal catalysts can also be used to initiate or accelerate the previously described hydrolysis or condensation reaction. Suitable metal catalyst systems are, for example, catalysts based on tin or titanium, such as titanium tetrabutoxide, dibutyltin dilaurate and dibutyltin bis(acetylacetonate).

According to the invention, the catalysts are preferably used in the quantitative ranges customary for catalysts. Since the catalysts accelerate the hydrolysis or condensation without being consumed themselves, the amounts selected to be used can be small.

Thus, the catalyst(s) can be used in a quantitative range of 0.0000001 to 2.0 wt. %, preferably 0.0001 to 1.5 wt. % and very particularly preferably 0.01 to 1.0 wt. %. Here, the specification in % by weight is based on the total amount of catalysts used set in relation to the total amount of organic $C_1$-$C_6$ alkoxy siloxanes plus water.

Production Method of the Mixture of Organic $C_1$-$C_6$ Alkoxy Siloxanes

To prepare the mixture of organic $C_1$-$C_6$ alkoxy siloxanes, different methods are in principle conceivable.

One possible production method is, for example, the following:

i) In a round-bottomed flask, an amount of organic $C_1$-$C_6$ alkoxy silane, for example methyltrimethoxysilane or methyltriethoxysilane is provided.

ii) The filled round-bottomed flask is provided with a stirrer and a thermometer.

iii) The round-bottomed flask is then clamped into a stirring apparatus and connected to the cooling system.

iv) The flask contents are brought to the desired temperature by means of oil bath, while stirring at 500 rpm.

v) When the desired temperature is reached, the amount of water with catalyst is metered into the round-bottomed flask over 3 minutes by means of a 100 ml dropping funnel. The dropping funnel is removed from the apparatus and replaced by a new dropping funnel which contains the previously calculated amount of a further organic $C_1$-$C_6$ alkoxy silane, for example (3-aminopropyl)-triethoxysilane.

vi) 10 to 60 minutes after completion of the addition of water plus catalyst, the second organic $C_1$-$C_6$ alkoxy silane is added dropwise.

vii) Where appropriate, a further amount of water and catalyst is added dropwise.

viii) Stirring continues for a further 30 to 240 minutes.

ix) The mixture of organic $C_1$-$C_6$ alkoxy siloxanes prepared in this way is filled into a leakproof container while still hot.

This production method is particularly suitable when the catalyst used is at least one acid, for example an acid from the group consisting of sulfuric acid, hydrochloric acid, phosphoric acid, maleic acid, citric acid, tartaric acid, malic acid, lactic acid, acetic acid, methanesulphonic acid, benzoic acid, malonic acid, oxalic acid and 1-hydroxyethane-1,1-diphosphonic acid.

Furthermore, this production method is also particularly suitable when at least one base, preferably from the group consisting of sodium hydroxide, potassium hydroxide, magnesium hydroxide and calcium hydroxide, are used as the catalyst.

As this production method shows, it is even preferred according to the invention and in the case of use of acids or bases as catalysts if the mixing of a first organic $C_1$-$C_6$ alkoxy silane with water and catalyst, which initiate the hydrolysis and precondensation of the first $C_1$-$C_6$ alkoxy silane, is additionally followed by the addition of a second organic $C_1$-$C_6$ alkoxy silane.

Mixtures of organic $C_1$-$C_6$ alkoxy siloxanes having particularly good cosmetic properties were obtained primarily when at least one organic $C_1$-$C_6$ alkoxy silane of formula (IV) was used in step I.) of the aforementioned method, and when at least one further organic $C_1$-$C_6$ alkoxy silanes of formula (I) was added in steps v.) or vi.) of the method.

In a further very particularly preferred embodiment, a method according to the invention is characterized in that the cosmetic agent comprises a mixture of organic $C_1$-$C_6$ alkoxy siloxanes, which mixture is obtained by (1) heating one or more organic $C_1$-$C_6$ alkoxy silanes of formula (IV) to a temperature from 30 to 80° C., preferably from 35 to 75° C., further preferably from 40 to 70° C. and very particularly preferably from 45 to 65° C., and mixing them with water and catalyst, then
(2) stirring the mixture obtained in step (1) for a period of 1 minute to 3 hours, then
(3) mixing the mixture obtained in step (2) with one or more organic $C_1$-$C_6$ alkoxy silanes of formula (I),
(4) where appropriate, mixing the mixture obtained in step (3) with further water and catalyst, and
(5) stirring the mixture obtained in step (3) or step (4) for a period of 30 minutes to 24 hours.

Step (4) is optional. In the context of step (4), the reaction mixture obtained in step (3) can be mixed once more with water and catalyst. If step (4) is performed, step (5) follows step (4). If step (4) is not carried out, step (5) follows step (3), i.e., in this case the mixture obtained in step (3) is stirred again in step (5) for a period of 30 minutes to 24 hours.

In a further, very especially preferred embodiment, a method according to the invention is characterized in that (5) the mixture obtained in step (3) or in step (4) is stirred for a period of 30 minutes to 24 hours, preferably from 40 to 18 hours, at a temperature from 30 to 80° C., preferably from 40 to 70° C.

In a further explicitly very particularly preferred embodiment, a method according to the invention is further characterized in that the cosmetic agent contains a mixture of organic $C_1$-$C_6$ alkoxy siloxanes, which mixture is obtained by (1) heating one or more organic $C_1$-$C_6$ alkoxy silanes of formula (IV) to a temperature from 30 to 80° C., preferably from 35 to 75° C., further preferably from 40 to 70° C. and very particularly preferably from 45 to 65° C., and mixing them with water and a catalyst from the group of the inorganic and organic acids, then
(2) stirring the mixture obtained in step (1) for a period of 1 minute to 3 hours, then
(3) mixing the mixture obtained in step (2) with one or more organic $C_1$-$C_6$ alkoxy silanes of formula (I), then
(4) mixing the mixture obtained in step (3) with further water and a catalyst from the group of the inorganic and organic bases, and
(5) stirring the mixture obtained in step (3) or step (4) for a period of 30 minutes to 24 hours.

In a further explicitly very particularly preferred embodiment, a method according to the invention is further characterized in that the cosmetic agent contains a mixture of organic $C_1$-$C_6$ alkoxy siloxanes, which mixture is obtained by (1) heating one or more organic $C_1$-$C_6$ alkoxy silanes of formula (IV) to a temperature from 30 to 80° C., preferably from 35 to 75° C., further preferably from 40 to 70° C. and very particularly preferably from 45 to 65° C., and mixing them with water and a catalyst from the group consisting of sulfuric acid, hydrochloric acid, phosphoric acid, maleic acid, citric acid, tartaric acid, malic acid, lactic acid, acetic acid, methanesulphonic acid, benzoic acid, malonic acid, oxalic acid and 1-hydroxyethane-1,1-diphosphonic acid, then
(2) stirring the mixture obtained in step (1) for a period of 1 minute to 3 hours, then
(3) mixing the mixture obtained in step (2) with one or more organic $C_1$-$C_6$ alkoxy silanes of formula (I), then
(4) mixing the mixture obtained in step (3) with further water and a catalyst from the group consisting of sodium hydroxide, potassium hydroxide, magnesium hydroxide and calcium hydroxide, and
(5) stirring the mixture obtained in step (3) or step (4) for a period of 30 minutes to 24 hours.

A further possible production method is the following:

i.) In a round-bottomed flask, an amount of organic $C_1$-$C_6$ alkoxy silanes, for example methyltrimethoxysilane and/or methyltriethoxysilane and/or (3-aminopropyl) triethoxysilane is provided.

Particularly preferably in this step a mixture of methyltrimethoxysilane and (3-aminopropyl) triethoxysilane, a mixture of methyltriethoxysilane and (3-aminopropyl) triethoxysilane or a mixture of ethyltriethoxysilane and (3-aminopropyl) triethoxysilane are provided.

ii.) The filled round-bottomed flask is provided with a stirrer and a thermometer.
iii.) The round-bottomed flask is then clamped into a stirring apparatus and connected to the cooling system.
iv.) The flask contents are brought to the desired temperature by means of oil bath, while stirring at 500 rpm.
v.) When the desired temperature is reached, the amount of water with catalyst is metered into the round-bottomed flask over 3 minutes by means of a 100 ml dropping funnel.
vi.) The mixture is stirred for a further 1 minute to 24 hours.
vii.) The mixture of organic $C_1$-$C_6$ alkoxy siloxanes prepared in this way is filled into a leakproof container while still hot or after cooling to room temperature.

This production method is particularly suitable when at least one base, preferably from the group consisting of sodium hydroxide, potassium hydroxide, magnesium hydroxide and calcium hydroxide, is used as the catalyst.

In a further embodiment, a particularly preferred method is characterized in that the cosmetic agent comprises a mixture of organic $C_1$-$C_6$ alkoxy siloxanes, which mixture is obtained by (1) mixing one or more organic $C_1$-$C_6$ alkoxy silanes of formula (I) and one or more organic $C_1$-$C_6$ alkoxy silanes of formula (IV) with one another,
(2) heating the mixture obtained in step (1) to a temperature from 30 to 80° C., preferably from 35 to 75° C., more preferably from 40 to 70° C. and most preferably from 45 to 65° C. and mixing it with water and catalyst, and then
(3) stirring the mixture obtained in step (2) for a period of 1 minute to 24 hours.

Mixtures of organic $C_1$-$C_6$ alkoxy siloxanes having particularly good cosmetic properties were obtained primarily when at least one organic $C_1$-$C_6$ alkoxy silane of formula (IV) and additionally at least one further organic $C_1$-$C_6$ alkoxy silanes of formula (I) were used in Step i.) of the aforementioned method.

In a further very particularly preferred embodiment, a method according to the invention is characterized in that the cosmetic agent comprises a mixture of organic $C_1$-$C_6$ alkoxy siloxanes, which mixture is obtained by (1) mixing one or more organic $C_1$-$C_6$ alkoxy silanes of formula (I) with one or more organic $C_1$-$C_6$ alkoxy silanes of formula (IV) and specifically hydrolyzing and precondensing them by adding water and catalyst.

In other words, a preferred method according to the invention is characterized in that the cosmetic agent comprises a mixture of organic $C_1$-$C_6$ alkoxy siloxanes, which mixture is obtained by (1) mixing one or more organic $C_1$-$C_6$ alkoxy silanes of formula (I) with one or more organic $C_1$-$C_6$ alkoxy silanes of formula (IV) and admixing them with water and catalyst.

In a further very especially preferred embodiment, the aforesaid method according to the invention is characterized in that (2) the mixture obtained in step (1) is stirred for a period of 1 minute to 24 hours, preferably from 2 to 24 hours, at a temperature from 30 to 80° C., preferably from 40 to 70° C.

The mixtures of organic $C_1$-$C_6$ alkoxy siloxanes produced in this way can alternatively also be referred to as a silane blend.

The organic $C_1$-$C_6$ alkoxy silanes used to prepare the mixture are partially hydrolyzed and condensed, so that dimeric, trimeric, oligomeric and in small parts probably also polymeric $C_1$-$C_6$ alkoxy siloxanes having higher molecular weight are present in the mixture. Since not all $C_1$-$C_6$ alkoxy groups bound to the silicon atoms are reacted, the mixture still has reactive functional groups which only react to the keratin material during subsequent application and can thus can continue to condense to form even higher polymeric systems. When these mixtures are used in cosmetic agents for the treatment of keratin material, very durable and uniform film or coatings can be produced on the keratin material in this way.

Method for Treating Keratin Material

The agents applied to keratin materials, in particular to human hair, are usually agents having a high water content. The cosmetic agent used in the method of the first subject matter of the invention is also a ready-to-use agent which can be anhydrous or water-poor, but can also have a high water content, i.e., a water content of more than 50 wt. %, preferably of more than 60 wt. % and particularly preferably of more than 70 wt. %.

Since the previously described mixture of organic $C_1$-$C_6$ alkoxy siloxanes comprise still reactive groups and, in the case of longer storage times, can be hydrolyzed by an excess of water, it is preferably made available to the user in the form of a water-poor concentrate and only shortly before use is mixed with a water-containing carrier and diluted in this way.

A method for treating keratin material, in particular human hair, is therefore particularly preferred which comprises the following steps in the following sequence:

(i) providing a mixture of organic $C_1$-$C_6$ alkoxy siloxanes the preparation of which has been described in detail above, (ii) mixing the mixture of organic $C_1$-$C_6$ alkoxy siloxanes with a cosmetic carrier, preferably an aqueous cosmetic carrier, in order to obtain a ready-to-use cosmetic agent, (iii) applying the cosmetic agent prepared in step (ii) to the keratin material, (iv) absorption of the agent applied in step (iii) into the keratin material, (v) rinsing the agent from the keratin material, (vi) where appropriate, applying a post-treatment agent to the keratin material, (vii) where appropriate, applying the post-treatment agent on the keratin material, and (viii) where appropriate, rinsing off the post-treatment agent from the keratin material.

In step (i) of the method, the mixture of organic $C_1$-$C_6$ alkoxy siloxanes is provided. This can take place, for example, in the form of a separately packaged panel or concentrate, which is preferably packaged in an airtight manner. Shortly before the application, the user or hairdresser in step (ii) can mix this concentrate with a cosmetic carrier, preferably an aqueous cosmetic carrier, in order to obtain a ready-to-use cosmetic agent.

For reasons of storage stability, the mixture of organic $C_1$-$C_6$ alkoxy siloxanes contains preferably no further cosmetic ingredients. However, the cosmetic carrier can contain various further ingredients.

The cosmetic ingredients which can optionally be used in the cosmetic carrier can be all suitable components for imparting further positive properties to the agent. For example, cosmetic ingredients from the group of thickening or film-forming polymers, the surface-active compounds from the group of nonionic, cationic, anionic or zwitterionic/amphoteric surfactants, the coloring compounds from the group of the pigments, the direct dyes, the oxidation dye precursors, the fatty components from the group of $C_8$-$C_{30}$ fatty alcohols, the hydrocarbon compounds, fatty acid esters, the acids and bases associated with the group of pH regulators, the perfumes, the preservatives, the plant extracts and the protein hydrolyzates can be added.

Mixing the $C_1$-$C_6$ alkoxy siloxane mixture and the cosmetic carrier can be effected, for example, by stirring or shaking. It is very particularly advantageous to assemble the two preparations separately in two containers, and then, before application, to transfer the entire amount of $C_1$-$C_6$ alkoxy siloxane mixture out of its container into the container in which the water-containing cosmetic carrier is located.

The $C_1$-$C_6$ alkoxy siloxane mixture and the in some cases water-containing cosmetic carrier can be mixed with one another in different quantitative ratios.

Particularly preferably, the $C_1$-$C_6$ alkoxy siloxane mixture in the form of a relatively highly concentrated, water-poor silane blend, which is virtually diluted by mixing with the aqueous cosmetic carrier. For this reason, it is very particularly preferred to mix the $C_1$-$C_6$ alkoxy siloxane mixture with an excess weight of cosmetic carrier. It is possible, for example, to mix 1 part by weight of siloxane mixture with 20 parts by weight of carriers, or to mix 1 part by weight of siloxane mixture with 10 parts by weight of carriers, or to mix 1 part by weight of siloxane mixture with 5 parts by weight of carriers.

In the context of certain embodiments, however, the use of an excess of $C_1$-$C_6$ alkoxy siloxane mixture, which is mixed with a deficit of cosmetic carrier, is also conceivable. It can therefore also be preferred if 1 part by weight of siloxane mixture is mixed with 1 part by weight of carriers, or to mix 1 part by weight of siloxane mixture with 0.5 parts by weight of carriers.

In step (iii) of the method, the ready-to-use cosmetic agent prepared in step (ii) is applied to the keratin material, in particular to the human hair. The application can take place with the aid of the gloved hand or else with the aid of a brush, a nozzle or an applicator.

Thereafter, in step (iv), the applied agent is allowed to act in or on the keratin material. Suitable here are exposure times of 30 to 60 minutes, preferably 1 to 30 minutes, more preferably 1 to 20 minutes, and most preferably 1 to 10 minutes.

Thereafter, in step (v) the agent is rinsed off of the keratin material, or the hair. The rinsing is preferably carried out only with tap water.

In steps (vi), (vii) and (viii), a post-treatment agent can optionally also be applied to the keratin material, allowed to soak in, and then, where appropriate rinsed out again.

It is very particularly preferred if the previously described keratin treatment method is a method for coloring human hair. In the context of this embodiment, the ready-to-use cosmetic agent applied in step (ii) particularly preferably additionally contains at least pigment and/or a direct dye.

In a further very particularly preferred embodiment, a method according to the invention is characterized in that it is a method for coloring human hair and in that the ready-to-use cosmetic agent applied in step (iii) additionally contains at least one pigment and/or a direct dye.

The use of a post-treatment agent can also be preferred, in particular, when the method for treating keratin material is a coloring method in which a coloring compound, such as, in particular, one in pigment, is to be applied to the keratin materials in a subsequent step.

In a further very particularly preferred embodiment, a method according to the invention is characterized in that it is a method for coloring hair and the post-treatment agent applied in step (vi) contains at least one pigment and/or a direct dye.

Pigment and/or a Direct Dye

In the course of the work leading to this invention, it was observed that the films formed on the keratin material have not only a good rubbing fastness but also a particularly high color intensity if a coloring compound from the group of the pigments and/or the direct dyes was applied in the method. The use of pigments has proven to be very particularly preferred.

The coloring compound(s) can be selected from the group of pigments and direct dyes, wherein the direct dyes can also be photochromic dyes and thermochromic dyes.

Pigments within the meaning of the present invention are understood to mean dyeing compounds which have a solubility of less than 0.5 g/L, preferably of less than 0.1 g/L, even more preferably of less than 0.05 g/L, at 25° C. in water. The method described below, for example, can be used to determine water solubility: 0.5 g of the pigment is weighed out in a beaker. A stir bar is added. Then one liter of distilled water is added. This mixture is heated to 25° C. while stirring with a magnetic stirrer for one hour. If still undissolved components of the pigment are visible in the mixture after this period, the solubility of the pigment is below 0.5 g/L. If the pigment-water mixture cannot be visually assessed due to the high intensity of the pigment that may be finely dispersed, the mixture is filtered. If a portion of undissolved pigments remains on the filter paper, the solubility of the pigment is below 0.5 g/L.

Suitable pigments may be of inorganic and/or organic origin.

In a preferred embodiment, an agent used in the method according to the invention is characterized in that it contains at least one dyeing compound from the group of inorganic and/or organic pigments.

Preferred color pigments are selected from synthetic or natural inorganic pigments. Inorganic color pigments of natural origin can be produced, for example, from chalk, ocher, umbra, green soil, burnt Sienna or graphite. Furthermore, black pigments such as, for example, iron oxide black, chromatic pigments such as, for example, ultramarine or iron oxide red, and also fluorescent or phosphorescent pigments, can be used as inorganic color pigments.

Colored metal oxides, hydroxides and oxide hydrates, mixed phase pigments, sulfur-containing silicates, silicates, metal sulfides, complex metal cyanides, metal sulfates, chromates and/or molybdates are particularly suitable. Particularly preferred color pigments are black iron oxide (CI 77499), yellow iron oxide (CI 77492), red and brown iron oxide (CI 77491), manganese violet (CI 77742), ultramarine (sodium aluminum sulphosilicates, CI 77007, Pigment Blue 29), chromium oxide hydrate (CI77289), Iron Blue (ferric ferrocyanide, CI77510) and/or carmine (cochineal).

According to the invention, coloring compounds from the group of pigments are also particularly preferably colored pearlescent pigments. These are usually based on mica and may be coated with one or more metal oxides. Mica is a phyllosilicate. The most important representatives of these silicates are muscovite, phlogopite, paragonite, biotite, lepidolite, and margarite. In order to produce the pearlescing pigments in conjunction with metal oxides, mica, primarily muscovite or phlogopite, is coated with a metal oxide.

In the context of a very particularly preferred embodiment, a method according to the invention is characterized in that the corresponding agent contains at least one coloring compound from the group of pigments selected from the group consisting of colored metal oxides, metal hydroxides, metal oxide hydrates, silicates, metal sulfides, complex metal cyanides, metal sulphates, bronze pigments and/or from mica-based colored pigments, which are coated with at least one metal oxide and/or a metal oxychloride.

As an alternative to natural mica, synthetic mica coated with one or more metal oxides(s) can also be used as a pearlescent pigment. Particularly preferred pearlescent pigments are based on natural or synthetic mica and are coated with one or more of the aforementioned metal oxides. The color of the respective pigments can be varied by varying the layer thickness of the metal oxide(s).

In a further preferred embodiment, a method according to the invention is characterized in that the corresponding agent contains at least one coloring compound from the group of pigments selected from the group of colored metal oxides, metal hydroxides, metal oxide hydrates, silicates, metal sulfides, complex metal cyanides, metal sulphates, bronze pigments and/or from mica-based colored pigments, which are coated with at least one metal oxide and/or one metal oxychloride.

In another preferred embodiment, a method according to the invention is characterized in that the corresponding agent contains at least one coloring compound selected from mica-based pigments, which is coated with one or more metal oxides from the group consisting of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, pigment blue 29), chromium oxide hydrate (CI 77289), chromium oxide (CI 77288) and/or iron blue (ferric ferrocyanide, CI 77510).

Examples of particularly suitable color pigments are commercially available, for example, under the trade names Rona®, Colorona®, Xirona®, Dichrona® and Timiron® from the company Merck, Ariabel® and Unipure® from the company Sensient, Prestige® from the company Eckart Cosmetic Colors, and Sunshine® from the company Sunstar.

Very particularly preferred color pigments with the trade name Colorona® are, for example:

Colorona Copper, Merck, MICA, CI 77491 (IRON OXIDES)
Colorona Passion Orange, Merck, Mica, CI 77491 (IRON OXIDES), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (IRON OXIDES), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)

Additional particularly preferred color pigments with the trade name Xirona® are, for example:

Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

In addition, particularly preferred color pigments with the trade name Unipure® are, for example:

Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica
Timiron Synwhite Satin, Merck, Synthetic Fluorphlogopite, Titanium Dioxide, Tin Oxide
Timiron Super Blue, Merck, Mica, CI 77891 (Titanium Dioxide)
Timiron Diamond Cluster MP 149, Merck, Mica, CI 77891 (Titanium dioxide)
Timiron Splendid Gold, Merck, CI 77891 (Titanium dioxide), Mica, Silica
Timiron Super Sulver, Merck, Mica, CI 77891 (Titanium dioxide)

Within the context of another embodiment, the agent used in the method according to the invention can also contain one or more dyeing compounds from the group of organic pigments.

The organic pigments according to the invention are correspondingly insoluble organic dyes or colored paints, which may be selected, for example, from the group of nitroso, nitro, azo, xanthene, anthraquinone, isoindolinone, isoindoline, quinacridone, perinone, perylene, diketopyrrolopyorrole, indigo, thioindido, dioxazine, and/or triarylmethane compounds.

Particularly well suited organic pigments can for example include carmine, quinacridone, phthalocyanine, sorghum, blue pigments with the Color Index numbers CI 42090, CI 69800, CI 69825, CI 73000, CI 74100 or CI 74160, yellow pigments with the Color Index numbers CI 11680, CI 11710, CI 15985, CI 19140, CI 20040, CI 21100, CI 21108, CI 47000 or CI 47005, green pigments with the Color Index numbers CI 61565, CI 61570 or CI 74260, orange pigments with the Color Index numbers CI 11725, CI 15510, CI 45370 or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, a method according to the invention is characterized in that the corresponding agent contains at least one coloring compound from the group of organic pigments which is selected from the group consisting of carmine, quinacridone, phthalocyanine, sorghum, blue pigments with the Color Index numbers CI 42090, CI 69800, CI 69825, CI 73000, CI 74100 or CI 74160, yellow pigments with the Color Index numbers CI 11680, CI 11710, CI 15985, CI 19140, CI 20040, CI 21100, CI 21108, CI 47000 or CI 47005, green pigments with the Color Index numbers CI 61565, CI 61570 or CI 74260, orange pigments with the Color Index numbers CI 11725, CI 15510, CI 45370 or CI 71105, and red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color lake. The term color lake within the meaning of the invention is understood to mean particles which comprise a layer of absorbed dyes, with the unit consisting of particles and dye being insoluble under the above-mentioned conditions. The particles may be, for example, inorganic substrates which may be aluminum, silica, calcium borosilicate, calcium aluminum borosilicate or aluminum.

For example, the alizarin color lake can be used as the color lake.

Owing to their excellent light and temperature resistance, the use of the aforementioned pigments in the agent according to the invention is particularly preferred. It is further preferred if the pigments used have a certain particle size. This particle size leads on the one hand to a uniform distribution of the pigments in the polymer film formed and, on the other hand, avoids a rough hair or skin feel after the application of the cosmetic agent. It is therefore advantageous according to the invention if the at least one pigment has an average particle size $D_{50}$ from 1.0 to 50 μm, preferably from 5.0 to 45 μm, preferably from 10 to 40 μm, in particular from 14 to 30 μm. The average particle size $D_{50}$ can be determined, for example, using dynamic light scattering (DLS).

Pigments with a specific shaping can also have been used to color the keratin material. For example, a pigment based on a lamellar and/or lenticular substrate plate can be used. Furthermore, dyeing is also possible based on a substrate plate which comprises a vacuum-metalized pigment.

In the context of another embodiment, a method according to the invention can be characterized in that the corresponding agent also comprises one or more dyeing compounds from the group of pigments based on a lamellar substrate plate, pigments based on a lenticular substrate plate, and vacuum-metalized pigments.

The substrate plates of this type have an average thickness of at most 50 nm, preferably less than 30 nm, particularly preferably at most 25 nm, for example at most 20 nm. The average thickness of the substrate plates is at least 1 nm, preferably at least 2.5 nm, particularly preferably at least 5 nm, for example at least 10 nm. Preferred ranges for the thickness of the substrate plates are 2.5 to 50 nm, 5 to 50 nm, 10 to 50 nm; 2.5 to 30 nm, 5 to 30 nm, 10 to 30 nm; 2.5 to 25 nm, 5 to 25 nm, 10 to 25 nm, 2.5 to 20 nm, 5 to 20 nm and 10 to 20 nm. Preferably, each substrate plate has as uniform a thickness as possible.

Due to the small thickness of the substrate plates, the pigment has a particularly high covering power.

The substrate plates have a monolithic structure. Monolithic in this context means consisting of a single self-contained unit without fractures, stratifications or inclusions, although structural changes may, however, occur within the substrate plates. The substrate plates are preferably composed homogeneously, i.e. there is no concentration gradient within the plates. In particular, the substrate plates are not composed in layers and do not have any particles distributed therein.

The size of the substrate plate can be matched to the respective application, in particular to the desired effect on the keratin material. As a rule, the substrate plates have a mean maximum diameter of approximately 2 to 200 μm, in particular approximately 5 to 100 μm.

In a preferred embodiment, the form factor (aspect ratio), expressed by the ratio of the average size to the average thickness, is at least 80, preferably at least 200, more preferably at least 500, particularly preferably more than 750. The average size of the uncoated substrate plates is understood to mean the d50 value of the uncoated substrate plates. Unless stated otherwise, the d50 value was determined with a Sympatec Helos-type device with Quixel wet dispersion. To prepare the sample, the sample to be investigated was pre-dispersed in isopropanol for a period of 3 minutes.

The substrate plates may be composed of any material that can be converted into the form of a plate.

They can be of natural origin, but can also be produced synthetically. Materials from which the substrate plates can be composed are, for example, metals and metal alloys, metal oxides, preferably aluminum oxide, inorganic compounds and minerals such as mica and (semi)precious stones, as well as plastics. Preferably, the substrate plates are made of metal (alloys).

Any metal suitable for metallic luster pigments is suitable as the metal. Such metals are, inter alia, iron and steel, and all air-resistant and water-resistant (semi) metals such as, for example, platinum, zinc, chromium, molybdenum and silicon, as well as alloys thereof such as aluminum bronzes and brass. Preferred metals are aluminum, copper, silver and gold. Preferred substrate plates are aluminum plates and brass plates, wherein substrate plates made of aluminum are particularly preferred.

Lamellar substrate plates are characterized by an irregularly structured edge and are also referred to as “cornflakes” due to their appearance.

Due to their irregular structure, pigments based on lamellar substrate plates produce a large amount of scattered light. In addition, pigments based on lamellar substrate plates do not completely cover the existing color of a keratin material, and effects analogous to natural graying can be achieved, for example.

Lenticular (=lens-shaped) substrate plates have a substantially round edge and are also referred to as “silver dollars” due to their appearance. Due to their regular structure, pigments based on lenticular substrate plates have the predominance of reflected light.

Vacuum metalized pigments (VMP) can be obtained, for example, by releasing metals, metal alloys or metal oxides of correspondingly coated films. They are characterized by a particularly small thickness of the substrate plates within a range of 5 to 50 nm and by a particularly smooth surface with increased reflectivity. Substrate plates which comprise a pigment metalized in a vacuum are also referred to as VMP substrate plates in the context of this application. VMP substrate plates of aluminum can be obtained, for example, by releasing aluminum from metalized films.

The substrate plates made of metal or metal alloy can be passivated, for example by anodizing (oxide layer) or chromating.

Uncoated lamellar, lenticular and/or VPM substrate plates, in particular those made of metal or metal alloy, reflect the incident light to a high degree and produce a light-dark flop, but no impression of color.

An impression of color can be produced, for example, from optical interference effects. Such pigments can be based on at least single-coated substrate plates. These manifest interference effects by superimposing differently refracted and reflected light beams.

Accordingly, preferred pigments are pigments based on a coated lamellar substrate plate. The substrate plate preferably has at least one coating B of a highly refractive metal oxide with a coating thickness of at least 50 nm. A coating A is preferably still between the coating B and the surface of the substrate plate. Optionally, another coating C, which is different from the underlying layer B, is on the layer B.

Suitable materials for coatings A, B and C are all substances that can be applied to the substrate plates in a film-like and permanent manner and, in the case of coatings A and B, have the required optical properties. In general, a coating of a part of the surface of the substrate plates is sufficient to obtain a pigment with a glossy effect. Thus, for example, only the upper and/or lower side of the substrate plates can be coated, wherein the side face(s) are omitted. Preferably, the entire surface of the optionally passivated substrate plates, including the side surfaces, is covered by coating B. The substrate plates are therefore completely enveloped by coating B. This improves the optical properties of the pigment and increases the mechanical and chemical resilience the pigments. The above also applies to layer A and preferably also to layer C, if present.

Although a plurality of coatings A, B and/or C can always be present, the coated substrate plates preferably each have only one coating A, B and, if present, C.

The coating B is composed of at least one highly refractive metal oxide. Highly refractive materials have a refractive index of at least 1.9, preferably at least 2.0, and particularly preferably at least 2.4. The coating B preferably comprises at least 95 wt. %, particularly preferably at least 99 wt. %, of highly refractive metal oxide(s).

The coating B has a thickness of at least 50 nm. The thickness of coating B is preferably not more than 400 nm, particularly preferably at most 300 nm.

Highly refractive metal oxides suitable for coating B are preferably selectively light-absorbing (i.e. colored) metal oxides such as iron(III) oxide (α- and γ-Fe2O3, red), cobalt (II) oxide (blue), chromium(III) oxide (green), titanium(III) oxide (blue, usually in a mixture with titanium oxynitrides and titanium nitrides) and vanadium(V) oxide (orange) and mixtures thereof. Also suitable are colorless, highly-refractive oxides such as titanium dioxide and/or zirconium oxide.

Coating B can contain a selectively absorbing dye, preferably 0.001 to 5 wt. %, particularly preferably 0.01 to 1 wt. %, in each case based on the total amount of the coating B. Organic and inorganic dyes which can be stably incorporated into a metal oxide coating are suitable.

The coating A preferably has at least one low-refractive metal oxide and/or metal oxide hydrate. Preferably, coating A comprises at least 95 wt. %, particularly preferably at least 99 wt. %, low-refractive metal oxide (hydrate). Low-refractive materials have a refractive index of at most 1.8, preferably at most 1.6.

The low-refractive metal oxides suitable for coating A include, for example, silicon (di)oxide, silicon oxide hydrate, aluminum oxide, aluminum oxide hydrate, boric oxide, germanium oxide, manganese oxide, magnesium oxide and mixtures thereof, with silicon dioxide being preferred. The coating A preferably has a thickness from 1 to 100 nm, particularly preferably 5 to 50 nm, in particular preferably 5 to 20 nm.

The distance between the surface of the substrate plates and the inner surface of coating B is preferably at most 100 nm, particularly preferably at most 50 nm, in particular preferably at most 20 nm. Because the thickness of coating A and therefore the distance between the surface of the substrate plates and coating B is in the range indicated above, it can be ensured that the pigments have a high covering power.

If the pigment has only one layer A based on a lamellar substrate plate, it is preferred that the pigment has a lamellar substrate plate of aluminum and a layer A of silicon dioxide. If the pigment has a layer A and a layer B based on a lamellar substrate plate, it is preferred that the pigment has a lamellar substrate plate of aluminum, a layer A of silicon dioxide, and a layer B of iron oxide.

According to a preferred embodiment, the pigments have another coating C of a metal oxide (hydrate) different from the underlying coating B. Suitable metal oxides are, for example, silicon (di)oxide, silicon oxide hydrate, aluminum oxide, aluminum oxide hydrate, zinc oxide, tin oxide, titanium dioxide, zirconium oxide, iron(III) oxide and chromium(III) oxide. Silicon dioxide is preferred.

The coating C preferably has a thickness of 10 to 500 nm, particularly preferably 50 to 300 nm. By providing the coating C, for example based on $TiO_2$, better interference can be achieved, while high covering power is maintained.

Layers A and C are in particular for corrosion protection as well as for chemical and physical stabilization. The layers A and C particularly preferably contain silicon dioxide or aluminum oxide which are applied by the sol gel method. This method comprises dispersing the uncoated lamellar substrate plates, or the lamellar substrate plates already coated with layer A and/or layer B, in a solution of a metal alkoxide such as tetraethyl orthosilicate or aluminum triisopropanolate (usually in a solution of organic solvent or a mixture of organic solvent and water with at least 50 wt. % organic solvent such as a C1 to C4 alcohol), and adding a weak base or acid for hydrolyzing the metal alkoxide, thereby forming a film of the metal oxide on the surface of the (coated) substrate plates.

Layer B can be produced, for example, by hydrolytic decomposition of one or more organic metal compounds and/or by precipitation of one or more dissolved metal salts and an optional subsequent post-treatment (for example, transferring formed hydroxide-containing layers into the oxide layers by tempering).

Although each of the coatings A, B and/or C can be composed of a mixture of two or more metal oxide (hydrates), each of the coatings is preferably composed of a metal oxide (hydrate).

The pigments based on coated lamellar or lenticular substrate plates or the pigments based on coated VMP substrate plates preferably have a thickness from 70 to 500 nm, particularly preferably 100 to 400 nm, in particular preferably 150 to 320 nm, for example 180 to 290 nm. Due to the small thickness of the substrate plates, the pigment has a particularly high covering power. The small thickness of the coated substrate plates is achieved in particular because the thickness of the uncoated substrate plates is low, but also because the thicknesses of the coatings A and, if present, C are set to the smallest possible value. The thickness of coating B determines the color impression of the pigment.

The adhesion and abrasion resistance of pigments based on coated substrate plates in the keratin material can be significantly increased by additionally modifying the outermost layer, depending on the structure of layer A, B or C, using organic compounds such as silanes, phosphoric acid esters, titanates, borates or carboxylic acids. The organic compounds are bonded to the surface of the outermost, preferably metal oxide-containing layer A, B or C. The outermost layer refers to the layer spatially furthest removed from the lamellar substrate plate. The organic compounds are preferably functional silane compounds which can bind to the metal oxide-containing layer A, B or C. These may be either monofunctional or bifunctional compounds. Examples of bifunctional organic compounds include methacryloxypropenyltrimethoxysilane, 3-methacryloxypropyltrimethoxysilane, 3-acryloxypropyltrimethoxysilane, 2-acryloxyethyltrimethoxysilane, 3-methacryloxypropyltriethoxysilane, 3-acryloxypropyltrimethoxysilane, 2-methacryloxyethyltriethoxysilane, 2-acryloxyethyltriethoxysilane, 3-methacryloxypropyltris(methoxyethoxy)silane, 3-methacryloxypropyltris(butoxyethoxy)silane, 3-methacryloxypropyltris(propoxy)silane, 3-methacryloxypropyltris(butoxy)silane, 3-acryloxypropyltris(methoxyethoxy)silane, 3-acryloxypropyltris(butoxyethoxy)silane, 3-acryl-oxypropyltris(butoxy)silane, vinyltrimethoxysilane, vinyltriethoxysilane, vinylethyldichlorosilane, vinylmethyldiacetoxysilane, vinylmethyldichlorosilane, vinylmethyldiethoxysilane, vinyltriacetoxysilane, vinyltrichlorosilane, phenylvinyldiethoxysilane, or phenylallyldichlorosilane. Furthermore, a modification with a monofunctional silane, in particular an alkylsilane or arylsilane, can take place. This has only one functional group which can bind covalently to the surface pigment based on coated lamellar substrate plates (i.e., to the outermost metal oxide-containing layer) or, when the covering is not complete, to the metal surface. The hydrocarbon functional group of the silane faces away from the pigment. Depending on the type and nature of the hydrocarbon functional group of the silane, a different degree of hydrophobicity of the pigment is achieved. Examples of such silanes are hexadecyltrimethoxysilane, propyltrimethoxysilane, etc. Particularly preferably, pigments based on silica-coated aluminum substrate plates are surface-modified with a monofunctional silane. Octyltrimethoxysilane, octyltriethoxysilane, hexadecyltrimethoxysilane and hexadecyltriethoxysilane are particularly preferred. As a result of the altered surface properties/hydrophobization, an improvement in terms of adhesion, abrasion resistance and orientation in the application can be achieved.

Suitable pigments based on a lamellar substrate plate comprise, for example, the pigments of the VISIONAIRE series by Eckart.

Pigments based on a lenticular substrate plate are available, for example, under the name of Alegrace® Gorgeous from the company Schlenk Metallic Pigments GmbH.

Pigments based on a substrate plate, which comprises a vacuum-metalized pigment, are available, for example, under the name of Alegrace® Marvelous or Alegrace® Aurous from the company Schlenk Metallic Pigment GmbH.

The compositions according to the invention may also contain one or more direct dyes as coloring compounds. Direct dyes are dyes, which attach directly to the hair and do not require an oxidative process to form the color. Direct dyes are usually nitrophenylenediamines, nitroaminophenols, azo dyes, anthraquinones, triarylmethane dyes, or indophenols.

Within the meaning of the present invention, the direct dyes have a solubility in water (760 mmHg) at 25° C. of more than 0.5 g/L and are therefore not to be regarded as pigments. Within the meaning of the present invention, the direct dyes preferably have a solubility in water (760 mmHg) at 25° C. of more than 1.0 g/L. Within the meaning of the present invention, the direct dyes particularly preferably have a solubility in water (760 mmHg) at 25° C. of more than 1.5 g/L.

Direct dyes can be divided into anionic, cationic, and non-ionic direct dyes.

In a further preferred embodiment, an agent according to the invention is characterized in that it contains at least one anionic, cationic and/or nonionic direct dye as a coloring compound.

In a further preferred embodiment, a method according to the invention is characterized in that the composition (B) and/or the composition (C) contains at least one coloring compound from the group of anionic, nonionic, and/or cationic direct dyes.

Suitable cationic direct dyes are, for example, Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 and Basic Red 76.

For example, non-ionic nitro dyes and quinone dyes and neutral azo dyes can be used as non-ionic direct dyes. Suitable non-ionic direct dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Anionic direct dyes are also referred to as acid dyes. Acid dyes are understood to be direct dyes that have at least one carboxylic acid group (—COOH) and/or a sulfonic acid group ($—SO_3H$). Depending on the pH, the protonated forms (—COOH, $—SO_3H$) of carboxylic acid or sulfonic acid groups are present in equilibrium with their deprotonated forms ($—COO^-$, $—SO_3$). The proportion of the protonated forms increases with a decreasing pH. If direct dyes are used in the form of their salts, thus the carboxylic acid groups or sulfonic acid groups are present in the deprotonated form and are neutralized to maintain the electroneutrality with corresponding stoichiometric equivalents of cations. According to the invention, acid dyes can also be used in the form of their sodium salts and/or their potassium salts.

Within the meaning of the present invention, the acid dyes have a solubility in water (760 mmHg) at 25° C. of more than 0.5 g/L and are therefore not to be regarded as pigments. Within the meaning of the present invention, the acid dyes preferably have a solubility in water (760 mmHg) at 25° C. of more than 1.0 g/L.

The alkaline earth salts (such as calcium salts and magnesium salts) or aluminum salts of acid dyes often have poorer solubility than the corresponding alkali metal salts. If the solubility of these salts is below 0.5 g/L (25° C., 760 mmHg), they do not fall under the definition of a direct dye.

An essential feature of the acid dyes is their ability to form anionic charges, wherein the carboxylic acid groups or sulfonic acid groups responsible for this are usually linked to different chromophoric systems. Suitable chromophoric systems are found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

For example, one or more compounds can be selected as particularly well-suited acid dyes from the following group: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow N° 10, Quinoline Yellow, E104, Food Yellow 13), Acid Yellow 9 (CI 13015), Acid Yellow 17 (CI 18965), Acid Yellow 23 (COLIPA no C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C. 015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; AC ID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Red 46, True Red D, FD&C Red no. 2, Food Red 9, Naphtholrot S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI CI 27290), Acid Red 87 (Eosin, CI 45380), Acid Red 92 (COLIPA no C. 53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C. 063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The water solubility of the anionic direct dyes can be determined, for example, in the following way. 0.1 g of the anionic direct dye are placed in a beaker. A stirrer is added. Then 100 ml of water are added. This mixture is heated to 25° C. with stirring on a magnetic stirrer. The mixture is stirred for 60 minutes. Thereafter, the aqueous mixture is visually assessed. If there are still undissolved functional groups, the amount of water is increased, for example in increments of 10 ml. Water is added until the amount of dye used has dissolved completely. If the dye-water mixture cannot be visually assessed due to the high intensity of the dye, the mixture is filtered. If a proportion of undissolved dyes remains on the filter paper, the solubility test is repeated with a greater amount of water. If 0.1 g of the anionic direct dye dissolve at 25° C. in 100 ml of water, the solubility of the dye is 1.0 g/L.

Acid Yellow 1 carries the name 8-hydroxy-5,7-dinitro-2-naphthalenesulfonic acid disodium salt and has a solubility in water of at least 40 g/L (25° C.).

Acid Yellow 3 is a mixture of the sodium salts of mono- and sissulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid; its water solubility is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3–carboxylic acid and readily soluble in water at 25° C.

Acid Orange 7 is the sodium salt of 4-[(2-hydroxy-1-naphthyl) azo] benzene sulphonate. Its water solubility is more than 7 g/L (25° C.).

Acid Red 18 is the trisodium salt of 7-hydroxy-8-[(E)-(4-sulfonato-1-naphthyldiazenyl)]-1,3-naphthalenedisulfonate and has a very high water solubility of more than 20 wt. %.

Acid Red 33 is the dianhydro salt of 5-amino-4-hydroxy-3-(phenylazo)-naphthalene-2,7-disulfonate; its water solubility is 2.5 g/L (25° C.).

Acid Red 92 is the disodium salt of 3,4,5,6-tetrachloro-2-(1,4,5,8-tetrabromo-6-hydroxy-3-oxanthene-9-yl) benzoic acid, the water solubility of which is specified with greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene} methyl)-benzenesulfonate and has a water solubility of more than 20 wt. % (25° C.).

Furthermore, thermochromic dyes can also be used. Thermochromism involves the property of a material to change its color reversibly or irreversibly depending on the temperature. This can be accomplished by changing both the intensity and/or the wavelength maximum.

Finally, it is also possible to use photochromic dyes. Photochrom ism involves the property of a material, depending on the irradiation with light, in particular UV light, to change its color reversibly or irreversibly. This can be accomplished by changing both the intensity and/or the wavelength maximum.

Multi-Component Packaging Unit (Kit of Parts)

To increase the user comfort, all preparations necessary for the hair treatment process can be provided to the user in the form of a multicomponent packaging unit (Kit-of-parts).

A further subject matter of the invention is a multi-component packaging unit (kit of parts) for treating keratin material, in particular human hair, which comprises, packaged separately from one another, a first packaging unit containing a cosmetic agent (A) and a second packaging unit containing a cosmetic preparation (B), where the cosmetic preparation (A) is a mixture of organic $C_1$-$C_6$ alkoxy siloxanes the preparation of which was described in claims 1 to 14, and the cosmetic preparation (B) represents a water-containing cosmetic carrier which preferably contains at least one fat component and/or at least one surfactant.

"Fatty components," within the context of the invention are understood to be organic compounds with a solubility in water of less than 1 wt. %, and preferably less than 0.1 wt. % at room temperature (22° C.) and atmospheric pressure (760 mmHg). The definition of fat constituents also explicitly includes only uncharged (i.e. non-ionic) compounds. Fat components have at least a saturated or unsaturated alkyl group with at least 12 carbon atoms. The molecular weight of the fat component is at most 5,000 g/mol, preferably at most 2,500 g/mol, and particularly preferably at most 1,000 g/mol. The fat components are either polyoxyalkylated or polyglycerylated compounds.

Most preferably, the fatty constituents are selected from the group of $C_{12}$-$C_{30}$ fatty alcohols, which contains $C_{12}$-$C_{30}$ fatty acid triglycerides, $C_{12}$-$C_{30}$ fatty acid monoglycerides, the $C_{12}$-$C_{30}$ fatty acid diglycerides and/or hydrocarbons.

$C_{12}$-$C_{30}$ fatty alcohols can be saturated, mono- or polyunsaturated, linear or branched fatty alcohols having 12 to 30 C atoms.

Examples of particularly preferred linear, saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol). Preferred linear, unsaturated fatty alcohols (9Z)-octadec-9-en-1-ol (oleyl alcohol), (9E)-octadec-9-en-1-ol (elaidyl alcohol), (9Z,12Z)-octadeca-9,12-diene-1-ol (linoleyl alcohol), (9Z,12Z,15Z) octadeca-9,12,15-trien-1-ol (linolenyl alcohol), gadoleyl alcohol ((9Z) eicos-9-en-1-ol), arachidone alcohol ((5Z8,8Z,11Z,14Z)-eicos-5,8,11,14,17-tetraen-1-ol), erucyl alcohol ((13Z)-docos-13-en-1-ol) and/or brassidyl alcohol ((13E)-docosen-1-ol). The preferred representatives of branched fatty alcohols are 2-octyl-dodecanol, 2-hexyl dodecanol and/or 2-butyl-dodecanol.

The term surfactants (T) is understood to mean interface-active substances which form adsorption layers on upper and boundary surfaces or can aggregate in volume phases to form micelle colloids or lyotropic mesophases. A distinction is made between anionic surfactants consisting of a hydrophobic functional group and a negatively charged hydrophilic head group, amphoteric surfactants which bear both a negative and a compensating positive charge, cationic surfactants which have a positively charged hydrophilic group in addition to a hydrophobic functional group, and non-ionic surfactants which have no charges but strong dipole moments and are strongly hydrated in aqueous solution.

In the context of a very particularly preferred embodiment, a method according to the invention is characterized in that the second preparation (B) contains at least one non-ionic surfactant.

Non-ionic surfactants contain, for example as a hydrophilic group, a polyol group, a polyalkylene glycol ether group or a combination of polyol and polyglycol ether. Such compounds include, for example

- addition products of 2 to 50 mol ethylene oxide and/or 0 to 5 mol propylene oxide to linear and branched fatty alcohols having 6 to 30 C atoms, the fatty alcohol polyglycol ethers or the fatty alcohol polypropylene glycol ethers or mixed fatty alcohol polyethers,
- addition products of 2 to 50 mol ethylene oxide and/or 0 to 5 mol propylene oxide to linear and branched fatty alcohols having 6 to 30 C atoms, the fatty acid polyglycol ethers or the fatty acid polypropylene glycol ethers or mixed fatty alcohol polyethers,
- addition products of 2 to 50 mol ethylene oxide and/or 0 to 5 mol propylene oxide to linear and branched alkyl phenols having 8 to 15 C atoms in the alkyl group, the alkyl phenol polyglycol ethers or the alkyl polypropylene glycol ethers or mixed alkyl phenol polyethers,
- addition products end-capped with a methyl- or $C_2$-$C_6$ alkyl functional group of 2 to 50 mol ethylene oxide alkyl and/or 0 to 5 mol propylene oxide to linear and branched fatty alcohols with 8 to 30 carbon atoms, to fatty acids with 8 to 30 carbon atoms, and to alkylphenols with 8 to 15 carbon atoms in the alkyl group, such as those available type under the trade names Dehydol® LS, Dehydol® LT (Cognis),
- $C_{12}$-$C_{30}$ fatty acid monoesters and diesters of addition products of 1 to 30 mol ethylene oxide to glycerol,
- addition products of 5 to 60 mol ethylene oxide to castor oil and hydrogenated castor oil,
- polyol fatty acid esters, such as the commercially available product Hydagen® HSP (Cognis) or Sovermol®—types (Cognis),
- alkoxylated triglycerides,
- alkoxylated fatty acid alkyl ester of the formula (Tnio-1)

$$R^1CO—(OCH_2CHR^2)_wOR^3 \quad \text{(Tnio-1)}$$

wherein $R^1CO$ is a linear or branched, saturated and/or unsaturated acyl functional group having 6 to 22 carbon atoms, $R^2$ is hydrogen or methyl, $R^3$ is linear or branched alkyl functional groups having 1 to 4 carbon atoms and w is a number from 1 to 20,

- amine oxides,
- hydroxy mixed ethers, as are described, for example, in DE-OS 19738866,
- sorbitan fatty acid esters and addition products of ethylene oxide to sorbitan fatty acid esters such as the polysorbates,
- sugar fatty acid esters and addition products of ethylene oxide to sugar fatty acid esters,
- addition products of ethylene oxide to fatty acid alkanolamides and fatty amines,
- sugar surfactants of the type of the alkyl and alkenyl oligoglycosides according to formula (E4-II), $$R^4O\text{-}[G]_p \quad \text{(Tnio-2)}$$

in which $R^4$ represents an alkyl group or alkenyl functional group having 4 to 22 carbon atoms, G represents a sugar functional group having 5 or 6 carbon atoms, and p represents numbers from 1 to 10. They can be obtained in accordance with the pertinent methods of preparative organic chemistry. The alkyl and alkenyl oligoglycosides can be derived from aldoses or ketoses having 5 or 6 carbon atoms, preferably from glucose. The preferred alkyl and/or alkenyl oligoglycosides are therefore alky and/or alkenyl oligoglucosides. The index number p in the general formula (Tnio-2) indicates the degree of oligomerization (DP), i.e., the distribution of mono- and oligoglycosides, and represents a number between 1 and 10. While p must always be an integer in the individual molecular and can especially assume the values p=1 to 6 here, for a certain alkyl oligoglycoside the value p is an analytically determined calculated quantity, which is usually a fraction. Alkyl and/or alkenyl oligoglycosides having an average degree of oligomerization p of 1.1 to 3.0 are preferably used. From the perspective of application technology, alkyl and/or alkenyl oligoglycosides whose degree of oligomerization is less than 1.7 and lies in particular between 1.2 and 1.4 are preferred. The alkyl or alkenyl functional group $R^4$ can be derived from primary alcohols having 4 to 11, preferably 8 to 10 carbon atoms. Typical examples include butanol, caproic alcohol, caprylic alcohol, capric alcohol and undecyl alcohol as well as the industrial mixtures thereof, as obtained for example by the hydrogenation of industrial fatty acid methyl esters or in the course of the hydrogenation of aldehydes in the Roelen oxosynthesis reaction. Alkyl oliglucosides with a $C_8$-$C_{10}$ chain length (DP=1 to 3) which accumulate as the first runnings in the separation, by means of distillation, of industrial $C_8$-$C_{18}$ coco fatty alcohol and which may be contaminated with a $C_{12}$ alcohol content of less than 6 wt. % and alkyl oligoglucosides based on industrial $C_{9/11}$ oxo alcohols (DP=1 to 3) are preferred. The alkyl or alkenyl functional group $R^{15}$ can furthermore also be derived from primary alcohols having 12 to 22, preferably 12 to 14 carbon atoms. Typical examples include lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and the industrial mixtures thereof, which can be obtained as described above. Alkyl oligoglucosides based on hardened $C_{12/14}$ coconut alcohol and having a DP of 1 to 3 are preferred.

Sugar surfactants of the fatty-acid-N-alkylpolyhydroxyalkyl amide type, a non-ionic surfactant of formula (Tnio-3), $$R^5CO—NR^6—[Z] \quad \text{(Tnio-3)}$$

in which $R^5CO$ represents an aliphatic acyl functional group having 6 to 22 carbon atoms, $R^6$ represents hydrogen, an alkyl or hydroxy alkyl functional group having 1 to 4 carbon atoms and [Z] represents a linear or branched polyhydroxyalkyl functional group having 3 to 12 carbon atoms and 3 to 10 hydroxyl groups. Fatty acid-N-alkylpolyhydroxyalkyl amides are known substances which can be conventionally obtained by the reductive amination of a reducing sugar with ammonia, an alkylamine or an alkanolamine and subsequent acylation with a fatty acid, a fatty acid alkyl ester or a fatty acid chloride. Fatty acid-N-alkylpolyhydroxyalkyl amides are preferably derived from reducing sugars, glucose in particular, having 5 or 6 carbon atoms. The preferred fatty acid-N-alkylpolyhydroxyalkyl amides are therefore fatty acid-N-alkyl glucamides represented by formula (Tnio-4):

$$R^7CO—(NR^8)—CH_2—[CH(OH)]_4—CH_2OH \quad \text{(Tnio-4)}$$

The use of glucamides of formula (Tnio-4), in which Fe represents hydrogen or an alkyl group and $R^7CO$ represents the acyl functional group of caproic acid, caprylic acid, capric acid, lauric acid, myristic acid, palmitic acid, palm oleic acid, stearic acid, isostearic acid, oleic acid, elaidic acid, petroselic acid, linoleic acid, linolenic acid, arachidic acid, gadoleic acid, behenic acid or erucic acid or industrial mixtures thereof is preferred. Fatty acid-N-alkyl glucamides of formula (Tnio-4) obtained by reductive amination of glucose with methylamine and subsequent acylation using lauric acid or $C_{12/14}$ coconut fatty acid or an appropriate derivative thereof are particularly preferred. Furthermore, the polyhydroxyalkyl amides may also be derived from maltose and palatinose.

The fat constituent and the surfactant(s) can be contained in preparation (B), based on the total weight of preparation (B), in quantitative ranges of 0.1 to 20 wt. %, preferably 1.0 to 10.0 wt. %.

The statements made about the method according to the invention apply mutatis mutandis in regard to other preferred embodiments of the multicomponent packaging unit according to the invention.

EXAMPLES

1. Preparation of Mixtures of Organic $C_1$-$C_6$ Alkoxy Siloxanes 1.1. Siloxane Mixture 1—Acid Catalysis In a 500 ml round-bottomed flask, 61.5 g of methyltriethoxysilane were initially provided and heated to 76° C. while stirring. Thereafter, 7.7 g of a 1% solution of sulphuric acid in water were added dropwise over a period of about 5 minutes. The mixture was stirred for a further 20 minutes. Thereafter, 30.8 g (3-aminopropyl) triethoxysilane was added dropwise over a period of about 20 minutes. The temperature of the reaction mixture rose to 76° C. After the end of the addition, the mixture was stirred at 78° C. for a further 20 minutes. Thereafter, the volatile components were distilled off under reduced pressure (255 mbar, 50° C.) and the reaction mixture was decanted into an airtight glass vessel.

1.2. Siloxane Mixture 2—Acid Catalysis

In a 500 ml round-bottomed flask, 85.0 g of hexyltrimethoxysilane were initially provided and heated to 50° C. while stirring. Then 8.0 g of a 1% solution of sulphuric acid in water were added dropwise over a period of about 5 minutes. The mixture was stirred for a further 20 minutes. Then 7.0 g (3-aminopropyl) triethoxysilane were added dropwise over a period of about 20 minutes. The temperature of the reaction mixture rose to 76° C. After the end of the addition, the mixture was stirred at 70° C. for a further 20 minutes. Thereafter, the volatile components were distilled off under reduced pressure (255 mbar, 50° C.) and the reaction mixture was decanted into an airtight glass vessel.

1.3. Siloxane Mixture 3—Acid and Base Catalysis

In a 500 ml round-bottomed flask, 61.5 g of methyltriethoxysilane were initially provided and heated to 50° C. while stirring. 2.3 g of a 1% solution of sulphuric acid in water were then added dropwise over a period of about 5 minutes. Stirring was then performed for an additional 20 minutes at 50° C. Thereafter, 30.8 g (3-aminopropyl) of triethoxysilane were added dropwise over a period of about 5 minutes. Subsequently, 5.4 g of a 1% solution of sodium hydroxide solution in water were added dropwise over a period of 5 minutes. Thereafter, the volatile components were distilled off under reduced pressure (255 mbar, 50° C.) and the reaction mixture was decanted into an airtight glass vessel.

1.4. Siloxane Mixture 4—Base Catalysis

In a 500 ml round-bottomed flask, 59.5 g of methyltriethoxysilane and 29.7 g of 3-aminopropyl) triethoxysilane were mixed with one another while stirring. This mixture was heated to 50° C. under further stirring. Thereafter, 10.8 g of a 5% solution of sodium hydroxide were added dropwise in water over a period of about 5 minutes. The temperature of the reaction mixture rose to 53° C. The mixture was stirred at 50° C. for a further 45 minutes and subsequently filled into an air-tight glass vessel.

2. Coloration

The following coloring agents were provided:

Preparation (A), Mixture of Organic $C_1$-$C_6$ Alkoxy Siloxanes

| | |
|---|---|
| Siloxane mixture 1 | 10 g |
| Siloxane mixture 2 | 10 g |
| Siloxane mixture 3 | 10 g |
| Siloxane mixture 4 | 10 g |

Preparation (B)

| | |
|---|---|
| Colorona Bordeaux, Merck, MICA, CI 77491 (IRON OXIDES) | 5.5 g |
| Hydroxyethyl cellulose (Natrosol 250 HR) | 1.0 g |
| Cetearyl alcohol | 1.5 g |
| Eumulgin B3 (Ceteareth-30) | 1.5 g |

-continued

| | |
|---|---|
| Water | ad 100 g |

The ready-to-use coloring agent was prepared in each case by shaking 10 g of preparation (A) and 100 g of preparation (B) (shaking for 3 minutes). A strand of hair (Kerling Euronaturhaar white) was then immersed in the ready-to-use coloring agent and left for 1 minute therein. Thereafter, excess agent was stripped from each hair strand. Subsequently, each hair strand was washed out with water and dried. Subsequently, the strands were visually evaluated under a daylight lamp. The following results were obtained:

| | |
|---|---|
| Preparation (A), siloxane mixture 1 + preparation (B) | Bordeaux red, high color intensity |
| Preparation (A), siloxane mixture 2 + preparation (B) | Bordeaux red, high color intensity |
| Preparation (A), siloxane mixture 3 + preparation (B) | Bordeaux red, high color intensity |
| Preparation (A), siloxane mixture 4 + preparation (B) | Bordeaux red, high color intensity |

The invention claimed is:

1. A method for treating keratin material, the method comprising:

applying a cosmetic agent to the keratin material;

rinsing the cosmetic agent from the keratin material after an exposure time; and applying a post-treatment agent to the keratin material after rinsing the cosmetic agent from the keratin material;

wherein the cosmetic agent comprises a mixture of organic $C_1$-$C_6$ alkoxy siloxanes and a cosmetic carrier, and wherein the mixture of organic $C_1$-$C_6$ alkoxy siloxanes is obtained by specifically hydrolyzing and precondensing one or more organic $C_1$-$C_6$ alkoxy silanes by adding (i) from 0.10 to 0.80 molar equivalents of water and (ii) catalyst, and the hydrolysis and precondensation is carried out in the absence of any solvent different from water.

2. The method according to of claim 1, wherein the one or more organic $C_1$-$C_6$ alkoxy silanes are represented by formula (I), (II), and/or (IV):

$$R_1R_2N\text{-}L\text{-}Si(OR_3)_a(R_4)_b \quad (I)$$

where $R_1$, $R_2$ represent, independently of one another, a hydrogen atom or a $C_1$-$C_6$ alkyl group, L represents a linear or branched, divalent $C_1$-$C_{20}$ alkylene group, $R_3$, $R_4$ represent, independently of one another, a $C_1$-$C_6$ alkyl group, a represents an integer from 1 to 3, and b represents the integer 3–a, $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

where

R5, R5', R5", R6, R6' and R6" represent, independently of one another, a $C_1$-$C_6$ alkyl group, A, A', A", A" and A" represent, independently of one another, a linear or branched, divalent $C_1$-$C_{20}$ alkylene group, and $R_7$ and $R_8$ represent, independently of one another, a hydrogen atom, a $C_1$-$C_6$ alkyl group, a hydroxy $C_1$-$C_6$ alkyl group, a $C_2$-$C_6$ alkenyl group, an amino $C_1$-$C_6$ alkyl group, or a group of formula (III), $$(A'''')\text{-}Si(R_6'')_{d''}(OR_5'')_{c''} \quad (III),$$

where c represents an integer from 1 to 3, d represents the integer 3–c, c' represents an integer from 1 to 3, d' represents the integer 3–c', c" represents an integer from 1 to 3, d" represents the integer 3–c', e represents 0 or 1, f represents 0 or 1, g represents 0 or 1, and h represents 0 or 1, wherein the at least one of the functional groups from e, f, g and h is different from 0, and $$(R_9)_mSi(OR_{10})_k \quad (IV),$$

where $R_9$ represents a $C_1$-$C_{12}$ alkyl group or a $C_2$-$C_{12}$ alkenyl group, $R_{10}$ represents a $C_1$-$C_6$ alkyl group, k represents an integer from 1 to 4, and m represents the number 4–k.

3. The method of claim 1, wherein the one or more organic $C_1$-$C_6$ alkoxy silanes are selected from the group consisting of:

methyltrimethoxysilane,
methyltriethoxysilane,
ethyltrimethoxysilane,
ethyltriethoxysilane,
hexyltrimethoxysilane,
hexyltriethoxysilane,
octyltrimethoxysilane,
octyltriethoxysilane,
dodecyltrimethoxysilane,
dodecyltriethoxysilane,
vinyltrimethoxysilane,
vinyltriethoxysilane,
tetramethoxysilane,
tetraethoxysilane,
(3-aminopropyl) triethoxysilane,
(3-aminopropyl) trimethoxysilane,
(2-aminoethyl)triethoxysilane,
(2-aminoethyl)trimethoxysilane,
(3-dimethylaminopropyl) triethoxysilane,
(3-dimethylaminopropyl) trimethoxysilane,
(2-dimethylaminoethyl)triethoxysilane, and
(2-dimethylaminoethyl)trimethoxysilane.

4. The method of claim 3, wherein the mixture is obtained using the one or more organic $C_1$-$C_6$ alkoxy silanes of formula (I) and the one or more organic $C_1$-$C_6$ alkoxy silanes of formula (IV) in a weight ratio of (I)/(IV) ranging from 1:1 to 1:10.

5. The method of claim 1, wherein the one or more organic $C_1$-$C_6$ alkoxy silanes are heated to a temperature ranging from 30 to 80° C. before the water and the catalyst are added.

6. The method of claim 1, wherein the molar equivalents of water (S–W) is calculated according to the formula:

$$S - W = \frac{\text{mol(water)}}{\text{mol(silanes)} \times n\text{(alkoxy)}}$$

where

S–W represents the molar equivalent of water, mol(water) represents a molar amount of water used, mol(silanes) represents the total molar amount of the one or more $C_1$-$C_6$ alkoxy silanes used, in the reaction, and n(alkoxy) represents a number of $C_1$-$C_6$ alkoxy groups per $C_1$-$C_6$ alkoxy silane.

7. The method of claim 1, wherein the catalyst is selected from the group of inorganic acids and organic acids.

8. The method of claim 1, wherein the catalyst is selected from the group of inorganic bases and organic bases.

9. The method of claim 3, wherein the mixture is obtained by:

(1) heating the one or more organic $C_1$-$C_6$ alkoxy silanes of formula (IV) to a temperature ranging from 30 to 80° C., and mixing with the water and the catalyst;

(2) stirring the mixture obtained in step (1) for a period ranging from 1 minute to 3 hours;

(3) mixing the mixture obtained in step (2) with the one or more organic $C_1$-$C_6$ alkoxy silanes of formula (I);

(4) mixing the mixture obtained in step (3) with additional water and catalyst; and (5) stirring the mixture obtained in step (4) for a period ranging from 30 minutes to 24 hours.

10. The method of claim 3, wherein the mixture is obtained by:

(1) mixing the one or more organic $C_1$-$C_6$ alkoxy silanes of formula (I) and the one or more organic $C_1$-$C_6$ alkoxy silanes of formula (IV);

(2) heating the mixture obtained in step (1) to a temperature ranging from 30 to 80° C., and mixing with the water and the catalyst; and (3) stirring the mixture obtained in step (2) for a period ranging from 1 minute to 24 hours.

11. The method of claim 1, wherein the keratin material is human hair, and wherein the cosmetic agent additionally comprises at least one pigment or a direct dye.

12. The method of claim 1, wherein the keratin material is human hair, and wherein the post-treatment agent comprises at least one pigment or a direct dye.

13. The method of claim 2, wherein a represents the number 3 and b represents the number 0.

14. The method of claim 2, wherein:

$R_5$ and $R_5'$ represent, independently of each other, a methyl group or an ethyl group, c and c' both represent the number 3, and d and d' represent the number 0.

15. The method of claim 1, wherein the cosmetic agent is selected from the group consisting of:

(3-aminopropyl) triethoxysilane, (3-aminopropyl) trimethoxysilane, (2-aminopropyl) triethoxysilane, (2-aminopropyl) trimethoxysilane, (3-dimethylaminopropyl) triethoxysilane, (3-dimethylaminopropyl) trimethoxysilane, (2-dimethylaminoethyl)triethoxysilane, (2-dimethylaminoethyl)trimethoxysilane, and any combination thereof.

16. The method of claim 3, wherein the mixture is obtained by:

(1) heating the one or more organic $C_1$-$C_6$ alkoxy silanes of formula (IV) to a temperature ranging from 30 to 80° C., and mixing with the water and the catalyst;

(2) stirring the mixture obtained in step (1) for a period ranging from 1 minute to 3 hours;

(3) mixing the mixture obtained in step (2) with the one or more organic $C_1$-$C_6$ alkoxy silanes of formula (I); and (4) stirring the mixture obtained in step (3) for a period ranging from 30 minutes to 24 hours.

17. The method of claim 1, wherein the cosmetic carrier is an aqueous solution.

18. The method of claim 17, wherein the cosmetic carrier further comprises one or more ingredients selected from the group consisting of thickening or film-forming polymers, nonionic surfactants, cationic surfactants, anionic surfactants, amphoteric surfactants, coloring pigments, coloring direct dyes, oxidation dye precursors, $C_8$-$C_{30}$ fatty alcohols, hydrocarbon compounds, fatty acid esters, pH regulators, perfumes, preservatives, plant extracts, and protein hydrolyzates.

* * * * *